US008193397B2

(12) United States Patent
Flynn et al.

(10) Patent No.: US 8,193,397 B2
(45) Date of Patent: Jun. 5, 2012

(54) HYDROFLUOROETHER COMPOUNDS AND PROCESSES FOR THEIR PREPARATION AND USE

(75) Inventors: Richard M. Flynn, Mahtomedi, MN (US); Michael G. Costello, Afton, MN (US); Daniel R. Vitcak, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 527 days.

(21) Appl. No.: 11/567,643

(22) Filed: Dec. 6, 2006

(65) Prior Publication Data

US 2008/0139683 A1 Jun. 12, 2008

(51) Int. Cl.
*C07C 21/18* (2006.01)
*C07C 19/08* (2006.01)
*F24D 1/00* (2006.01)
*C08J 9/00* (2006.01)
*C08J 9/12* (2006.01)
*B26F 3/00* (2006.01)
*C08F 2/00* (2006.01)

(52) U.S. Cl. ............ 570/142; 521/82; 237/81; 83/177; 526/206

(58) Field of Classification Search .............. 568/685; 570/142; 521/82; 237/81; 83/177; 526/206
See application file for complete search history.

(56) References Cited

U.S. PATENT DOCUMENTS

| 2,713,593 | A | | 7/1955 | Brice et al. | |
|---|---|---|---|---|---|
| 3,342,777 | A | * | 9/1967 | Howard, Jr. .................. | 528/220 |
| 3,903,012 | A | | 9/1975 | Brandreth | |
| 3,962,460 | A | | 6/1976 | Croix et al. | |
| 4,024,192 | A | * | 5/1977 | Benninger et al. ............ | 568/669 |
| 4,067,884 | A | * | 1/1978 | Martini ......................... | 549/378 |
| 4,136,121 | A | * | 1/1979 | Martini et al. ................ | 568/397 |
| 4,143,078 | A | * | 3/1979 | Gibbs et al. ................... | 570/142 |
| 4,169,807 | A | | 10/1979 | Zuber | |
| 4,172,851 | A | * | 10/1979 | Childs .......................... | 568/397 |
| 4,275,225 | A | * | 6/1981 | Krespan ....................... | 560/174 |
| 4,576,752 | A | | 3/1986 | Krespan | |
| 4,736,045 | A | | 4/1988 | Drakesmith et al. | |
| 5,104,034 | A | | 4/1992 | Hansen et al. | |
| 5,125,978 | A | | 6/1992 | Flynn et al. | |
| 5,182,342 | A | | 1/1993 | Feiring et al. | |
| 5,210,106 | A | | 5/1993 | Dams et al. | |
| 5,539,008 | A | | 7/1996 | Dams et al. | |
| 5,648,560 | A | | 7/1997 | Marraccini et al. | |
| 5,696,308 | A | * | 12/1997 | Burgess et al. ............... | 570/142 |
| 5,750,797 | A | | 5/1998 | Vitcak et al. | |
| 5,925,611 | A | | 7/1999 | Flynn et al. | |
| 6,013,795 | A | * | 1/2000 | Manzara et al. .............. | 544/106 |
| 6,023,002 | A | * | 2/2000 | Behr et al. .................... | 568/685 |
| 6,046,368 | A | * | 4/2000 | Lamanna et al. ............. | 568/683 |
| 6,080,448 | A | | 6/2000 | Leiner et al. | |
| RE37,119 | E | | 4/2001 | Sherwood | |
| 6,303,080 | B1 | * | 10/2001 | Tuma ............................. | 422/38 |
| 6,313,359 | B1 | * | 11/2001 | Tung et al. ..................... | 570/142 |
| 6,361,713 | B1 | * | 3/2002 | Moore et al. .................. | 252/194 |
| 6,362,379 | B2 | | 3/2002 | Moore et al. | |
| 6,374,907 | B1 | | 4/2002 | Tousignant et al. | |
| 6,394,107 | B1 | * | 5/2002 | Kesari et al. ................. | 134/22.1 |
| 6,399,729 | B1 | | 6/2002 | Farnham et al. | |
| 6,407,282 | B1 | | 6/2002 | Murata et al. | |
| 6,573,235 | B1 | * | 6/2003 | Surbled et al. ................ | 512/1 |
| 6,759,374 | B2 | | 7/2004 | Milbrath et al. | |
| 6,953,082 | B2 | * | 10/2005 | Costello et al. .............. | 165/80.4 |
| 7,385,089 | B2 | * | 6/2008 | Costello et al. ............... | 568/413 |
| 2002/0001710 | A1 | | 1/2002 | Kang et al. | |
| 2002/0094944 | A1 | | 7/2002 | Flynn et al. | |
| 2003/0019841 | A1 | * | 1/2003 | Kesari et al. .................. | 216/67 |
| 2003/0027732 | A1 | * | 2/2003 | Howell et al. ................. | 508/579 |
| 2003/0089877 | A1 | * | 5/2003 | Rivers et al. .................. | 252/6 |
| 2004/0192974 | A1 | * | 9/2004 | Navarrini et al. ............. | 568/677 |
| 2004/0267053 | A1 | * | 12/2004 | Okazoe et al. ................ | 568/449 |
| 2005/0224747 | A1 | * | 10/2005 | Costello et al. ................ | 252/70 |
| 2006/0068283 | A1 | * | 3/2006 | Segawa et al. ................ | 429/200 |
| 2006/0128821 | A1 | * | 6/2006 | Owens et al. .................. | 521/79 |
| 2006/0205172 | A1 | * | 9/2006 | Gerlach et al. ................ | 438/401 |
| 2007/0015865 | A1 | * | 1/2007 | Hintzer et al. ................ | 524/544 |
| 2007/0051916 | A1 | * | 3/2007 | Flynn et al. .................... | 252/71 |
| 2007/0072985 | A1 | * | 3/2007 | Hintzer et al. ................ | 524/544 |
| 2007/0163710 | A1 | * | 7/2007 | Costello et al. ............... | 156/332 |
| 2008/0139683 | A1 | * | 6/2008 | Flynn et al. .................... | 521/114 |
| 2008/0269512 | A1 | * | 10/2008 | Lovis et al. .................... | 552/546 |

FOREIGN PATENT DOCUMENTS

| DE | 1294949 | 1/1968 |
|---|---|---|
| DE | 25 31 511 | 2/1977 |
| DE | 42 13 642 | 10/1993 |
| EP | 0 404 076 | 12/1990 |
| EP | 0 496 415 A1 | 7/1992 |
| FR | 2287432 | 6/1976 |
| JP | 2006-290779 | 10/2006 |
| WO | WO 84/02909 | 8/1984 |

OTHER PUBLICATIONS

Research Disclosures, No. 40576, p. 81 (Jan. 1998).
R,E. Banks, *Preparation, Properties and Industrial Applications of Organofluorine Compounds*, pp. 19-43, Halsted Press, New York (1982). Zapevalova et al., "Selective photolysis of the fluorides of perfluoroalkanecarboxylic keto acids," J. Org. Chem. USSR (Eng. Transl), vol. 14, No. 5, 1978, pp. 900-903, XP009098799.
Tonelli, C. et al., "Photolysis of perfluoroacyl fluorides," Journal of Fluorine Chemistry, Elsevier Sequoia, Lausanne, CH, vol. 101, No. 1, Jan. 2000, pp. 117-123, XP004244505, ISSN: 0022-1139.
Siegemund et al., "Fluorine Compounds, Organic" 2005, Ullmann's Encyclopedia of Industrial Chemistry, XP002476921.

* cited by examiner

*Primary Examiner* — Mark Eashoo
*Assistant Examiner* — Liam Heincer
(74) *Attorney, Agent, or Firm* — Lucy C. Weiss; Ann Kulprathipanja

(57) ABSTRACT

A hydrofluoroether compound comprises two terminal, independently fluoroalkyl or perfluoroalkyl groups and an intervening oxytetrafluoroethylidene moiety (—OCF(CF$_3$)—) bonded through its central carbon atom to an alkoxy- or fluoroalkoxy-substituted fluoromethylene moiety (—CF (OR)—), each of the terminal groups optionally comprising at least one catenated heteroatom.

16 Claims, No Drawings

US 8,193,397 B2

HYDROFLUOROETHER COMPOUNDS AND PROCESSES FOR THEIR PREPARATION AND USE

FIELD

This invention relates to partially-fluorinated ether compounds. In other aspects, this invention also relates to processes for preparing partially-fluorinated ether compounds and to processes for their use.

BACKGROUND

Hydrofluoroether compounds (HFEs) comprise a class of commercially valuable chemical compounds. In a number of applications, hydrofluoroethers have been found to be useful as replacements for chlorofluorocarbons (CFCs), which are currently disfavored and regulated due to the adverse effects that CFCs are believed to have on the environment. Unlike CFCs, hydrofluoroether compounds that contain fluorine as the only halogen have essentially no effect on the earth's ozone layer. Such hydrofluoroether compounds are thus said to exhibit an "ozone depletion potential" of zero. In addition, such HFEs are typically more easily degraded within the earth's atmosphere, which results in a low global warming potential.

Hydrofluoroether compounds have been prepared by various different methods including, for example, alkylation of perfluorinated acid fluorides (prepared by electrochemical fluorination or by direct fluorination), alkylation of perfluorinated ketones (prepared by reaction of perfluorinated acid fluorides and perfluorinated olefins), and photooxidation of tetrafluoroethylene (TFE) followed by reductive stabilization. Such methods have various advantages and disadvantages. For example, the latter method requires the handling of a relatively hazardous reagent, TFE, and also provides a broad product mixture that generally requires extensive purification. Such methods also have generally not been suitable for the production of some classes of branched HFEs (due to the difficulty of alkylation of certain branched perfluoroketones).

SUMMARY

In view of an increasing demand for environmentally friendly chemical compounds (preferably, compounds having an ozone depletion potential of zero and/or a low global warming potential), we recognize that there exists an ongoing need for HFEs that can meet the performance requirements of a variety of different applications (for example, boiling points of 150° C. or higher), as well as for efficient and cost-effective processes for their preparation. Such processes will preferably be capable of flexibly and controllably producing hydrofluoroether compounds having tailored structures and physical properties, without producing a broad product mixture.

Briefly, in one aspect, this invention provides a hydrofluoroether compound comprising two terminal, independently fluoroalkyl or perfluoroalkyl groups and an intervening oxytetrafluoroethylidene moiety (—OCF(CF$_3$)—) bonded through its central carbon atom to an alkoxy- or fluoroalkoxy-substituted fluoromethylene moiety (—CF(OR)—), each of the terminal groups optionally comprising at least one catenated (that is, in-chain) heteroatom. Preferably, the fluoromethylene moiety is alkoxy-substituted, and the terminal groups are independently selected from perfluoroalkyl groups that optionally contain at least one catenated heteroatom.

It has been discovered that a versatile new class of hydrofluoroether compounds can be produced in good yield by a simple process comprising the reaction of a fluorochemical acid fluoride with a fluoro- or perfluorovinyl ether to form a branched fluorochemical ketone, followed by the reaction of the branched fluorochemical ketone with an anhydrous alkali metal fluoride or anhydrous silver fluoride (preferably, in an anhydrous polar, aprotic solvent) to form a fluorochemical alkoxide that can then be alkylated (for example, using dialkyl sulfates). By varying the structure of the starting fluorochemical acid fluoride and fluoro- or perfluorovinyl ether, HFEs having tailored structures and physical properties can be controllably obtained.

Surprisingly, the alkylation reaction is facile, even when the fluorochemical ketone comprises branched moieties on both sides of (and adjacent to) its carbonyl group (that is, even when the fluorochemical ketone contains a branched terminal group, in addition to its tetrafluoroethylidene moiety). This is in stark contrast with the corresponding fluorochemical ketones obtained by reacting the same fluorochemical acid fluoride with the corresponding perfluoroolefin (rather than the fluoro- or perfluorovinyl ether). Such fluorochemical ketones can be alkylated only with difficulty to provide relatively much lower yields.

The HFEs of the invention can be used in a number of different applications including, for example, use as a solvent in coating deposition, as a cleaning or drying fluid, as a dry cleaning fluid, as a polymerization medium, as a document preservation medium, as a heat transfer agent, as a cell size regulator for use in foam blowing, as a heat transfer agent for use in vapor phase soldering, and as a metal working agent in the cutting or forming of metals. At least some of the HFEs exhibit unexpectedly high thermal stabilities, making them particularly useful in high temperature applications. At least some of the HFEs boil above 100° C. yet also exhibit surprisingly good low temperature viscosity characteristics. Thus, at least some embodiments of the invention meet the above-described, ongoing need for HFEs that can meet the performance requirements of a variety of different applications (as well as the need for efficient and cost-effective processes for their preparation).

In another aspect, this invention also provides fluorochemical ketone compounds useful in preparing the hydrofluoroether compounds of the invention. Such fluorochemical ketone compounds comprise two terminal, independently fluoroalkyl or perfluoroalkyl groups and an intervening oxytetrafluoroethylidene moiety (—OCF(CF$_3$)—) bonded through its central carbon atom to a carbonyl group, at least one of the terminal groups comprising at least one catenated (that is, in-chain) nitrogen atom. Preferably, at least one of the terminal groups comprises at least one perfluoromorpholino moiety.

In another aspect, this invention also provides a process for preparing the hydrofluoroether compounds comprising (a) reacting at least one fluorochemical (preferably, perfluorinated) acid fluoride with at least one fluoro- or perfluorovinyl (preferably, perfluorovinyl) ether to form at least one fluorochemical ketone (preferably, perfluoroketone) comprising two terminal, independently fluoroalkyl or perfluoroalkyl groups and an intervening oxytetrafluoroethylidene moiety (—OCF(CF$_3$)—) bonded through its central carbon atom to a carbonyl group, each of the terminal groups optionally comprising at least one catenated (that is, in-chain) heteroatom; (b) reacting the fluorochemical ketone compound with at least one fluoride source to form at least one fluorochemical (preferably, perfluorinated) alkoxide; and (b) reacting the fluorochemical alkoxide with at least one alkylating agent to form at least one hydrofluoroether compound.

In still other aspects, this invention provides the following processes for using the hydrofluoroether compounds of the invention:

A process for removing a contaminant (for example, an oil or grease, a particulate, or water) from an article comprising contacting the article with a composition comprising at least one hydrofluoroether compound of the invention.

A process for preparing a foamed plastic comprises vaporizing a blowing agent mixture in the presence of at least one foamable polymer or the precursors of at least one foamable polymer, the blowing agent mixture comprising at least one hydrofluoroether compound of the invention.

A process for vapor phase soldering comprising melting solder by immersing at least one component that comprises solder in a body of fluorinated liquid vapor that comprises at least one hydrofluoroether compound of the invention.

A process for transferring heat comprising transferring heat between a heat source and a heat sink through the use of a heat transfer agent comprising at least one hydrofluoroether compound of the invention.

A process for depositing a coating on a substrate comprising applying to at least a portion of at least one surface of the substrate a composition comprising (a) a solvent composition comprising at least one hydrofluoroether compound of the invention; and (b) at least one coating material (for example, a fluorinated polyether or a document preservation material) that is soluble or dispersible in the solvent composition.

A process for metal, cermet, or composite working comprising applying a working fluid to a metal, cermet, or composite workpiece and tool, the working fluid comprising at least one hydrofluoroether compound of the invention and at least one lubricious additive.

A polymerization process comprising polymerizing at least one monomer (preferably, a fluorine-containing monomer) in the presence of at least one polymerization initiator and at least one hydrofluoroether compound of the invention.

DETAILED DESCRIPTION

Definitions

As used in this patent application:

"catenated heteroatom" means an atom other than carbon (for example, oxygen, nitrogen, or sulfur) that is bonded to carbon atoms in a carbon chain so as to form a carbon-heteroatom-carbon chain;

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated; and

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

Hydrofluoroether Compounds

The novel compounds of the invention comprise two terminal, independently fluoroalkyl or perfluoroalkyl groups and an intervening oxytetrafluoroethylidene moiety (—OCF($CF_3$)—) bonded through its central carbon atom to an alkoxy- or fluoroalkoxy-substituted fluoromethylene moiety (—CF(OR)—), each of the terminal groups optionally comprising at least one catenated (that is, in-chain) heteroatom. Preferably, the fluoromethylene moiety is alkoxy-substituted, and the terminal groups are independently selected from perfluoroalkyl groups that optionally contain at least one catenated heteroatom.

A class of the compounds of the invention is that which can be represented by the following general formula (I):

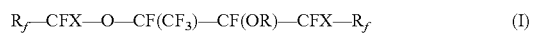

$$R_f\text{—CFX—O—CF(CF}_3\text{)—CF(OR)—CFX—}R_f \quad (I)$$

wherein each $R_f$ is independently a fluorine atom or a perfluoroalkyl group that is linear, branched, cyclic, or a combination thereof, that optionally contains at least one catenated heteroatom, and that optionally comprises a terminal moiety selected from —$CF_2H$, —$CFHCF_3$, and —$CF_2OCH_3$; each X is independently a fluorine atom or a perfluoroalkyl group that is linear, branched, cyclic, or a combination thereof and that has from one to about six carbon atoms; and R is an alkyl or fluoroalkyl group that is linear, branched, cyclic, or a combination thereof and that optionally contains at least one catenated heteroatom. Preferably, each $R_f$ is independently a fluorine atom or a perfluoroalkyl group that is linear or branched, that optionally contains at least one catenated heteroatom, and that has from one to about eight carbon atoms (more preferably, from one to about four carbon atoms); each X is independently a fluorine atom or a perfluoroalkyl group that is linear or branched and that has from one to about three carbon atoms (more preferably, a fluorine atom or a perfluoromethyl group); and R is an alkyl or fluoroalkyl group that is linear or branched and that has from one to about eight carbon atoms (more preferably, an alkyl group having from one to about four carbon atoms; most preferably, an ethyl or methyl group).

Representative examples of the hydrofluoroether compounds of the invention include the following, where R is selected from $CH_3$, $C_2H_5$, $C_3H_7$, $C_4H_9$, $CH_2CF_3$, and $CH_2CF_2CF_2H$:

$CF_3OCF(CF_3)CF(OR)CF_3$, $CF_3OCF(CF_3)CF(OR)C_2F_5$ $CF_3OCF(CF_3)CF(OR)CF_2CF_2CF_3$, $CF_3OCF(CF_3)CF(OR)CF(CF_3)_2$ $CF_3OCF(CF_3)CF(OR)C_4F_9$, $CF_3OCF(CF_3)CF(OR)CF(CF_3)OCF_3$ $CF_3OCF(CF_3)CF(OR)CF(CF_3)OC_3F_7$, $CF_3OCF(CF_3)CF(OR)CF_2CF_2OCF_3$ $CF_3OCF(CF_3)CF(OR)CF_2CF_2H$, $CF_3OCF(CF_3)CF(OR)CF_2CF_2OCH_3$,

$C_2F_5OCF(CF_3)CF(OR)CF_3$, $C_2F_5OCF(CF_3)CF(OR)C_2F_5$ $C_2F_5OCF(CF_3)CF(OR)CF_2CF_2CF_3$, $C_2F_5OCF(CF_3)CF(OR)CF(CF_3)_2$ $C_2F_5OCF(CF_3)CF(OR)C_4F_9$, $C_2F_5OCF(CF_3)CF(OR)CF(CF_3)OC_3F_7$ $C_2F_5OCF(CF_3)CF(OR)CF_2CF_2OCF_3$, $C_2F_5OCF(CF_3)CF(OR)CF_2CF_2H$ $C_2F_5OCF(CF_3)CF(OR)CF_2CF_2OCH_3$, $C_2F_5OCF(CF_3)CF(OR)CF(CF_3)OC_2F_5$

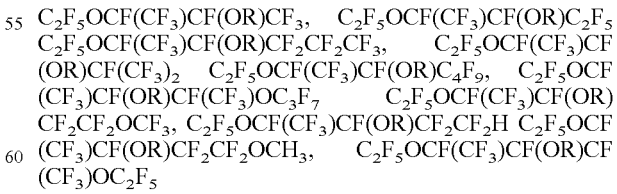

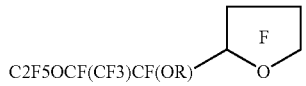

C2F5OCF(CF3)CF(OR)CF2— 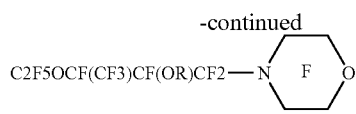

CF₃CF₂CF₂OCF(CF₃)CF(OR)CF₃, CF₃CF₂CF₂OCF(CF₃)CF(OR)C₂F₅ CF₃CF₂CF₂OCF(CF₃)CF(OR)CF₂CF₂CF₃, CF₃CF₂CF₂OCF(CF₃)CF(OR)CF(CF₃)₂ CF₃CF₂CF₂OCF(CF₃)CF(OR)C₄F₉, CF₃CF₂CF₂OCF(CF₃)CF(OR)CF(CF₃)OC₃F₇ CF₃CF₂CF₂OCF(CF₃)CF(OR)CF₂CF₂OCF₃ CF₃CF₂CF₂OCF(CF₃)CF(OR)CF₂CF₂H CF₃CF₂CF₂OCF(CF₃)CF(OR)CF₂CF₂OCH₃

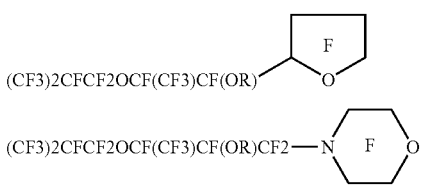

CF₃CF₂CF₂CF₂OCF(CF₃)CF(OR)CF₃,
CF₃CF₂CF₂CF₂OCF(CF₃)CF(OR)CF₂CF₃
CF₃CF₂CF₂CF₂OCF(CF₃)CF(OR)CF₂CF₂CF₃
CF₃CF₂CF₂CF₂OCF(CF₃)CF(OR)CF(CF₃)₂,
CF₂CF₂CF₂CF₂OCF(CF₃)CF(OR)C₄F₉
CF₂CF₂CF₂CF₂OCF(CF₃)CF(OR)CF(CF₃)OC₃F₇
CF₂CF₂CF₂CF₂OCF(CF₃)CF(OR)CF₂CF₂OCF₃
CF₂CF₂CF₂CF₂OCF(CF₃)CF(OR)CF₂CF₂H
CF₂CF₂CF₂CF₂OCF(CF₃)CF(OR)CF₂CF₂OCH₃
CF₂CF₂CF₂CF₂OCF(CF₃)CF(OR)CF(CF₃)OC₄F₉

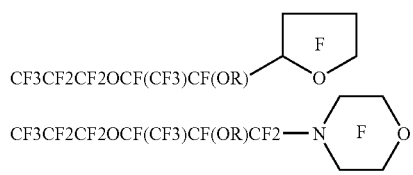

(CF₃)₂CFCF₂OCF(CF₃)CF(OR)CF₃, (CF₃)₂CFCF₂OCF(CF₃)CF(OR)CF₂CF₃ (CF₃)₂CFCF₂OCF(CF₃)CF(OR)CF₂CF₂CF₃ (CF₃)₂CFCF₂OCF(CF₃)CF(OR)CF(CF₃)₂, (CF₃)₂CFCF₂OCF(CF₃)CF(OR)C₄F₉ (CF₃)₂CFCF₂OCF(CF₃)CF(OR)CF(CF₃)OC₃F₇ (CF₃)₂CFCF₂OCF(CF₃)CF(OR)CF₂CF₂OCF₃ (CF₃)₂CFCF₂OCF(CF₃)CF(OR)CF₂CF₂H (CF₃)₂CFCF₂OCF(CF₃)CF(OR)CF₂CF₂OCH₃ (CF₃)₂CFCF₂OCF(CF₃)CF(OR)CF(CF₃)OC₄F₉

CF₃OCF₂CF₂CF₂OCF(CF₃)CF(OR)CF₃
CF₃OCF₂CF₂CF₂OCF(CF₃)CF(OR)CF₂CF₃
CF₃OCF₂CF₂CF₂OCF(CF₃)CF(OR)CF₂CF₂CF₃
CF₃OCF₂CF₂CF₂OCF(CF₃)CF(OR)CF(CF₃)₂
CF₃OCF₂CF₂CF₂OCF(CF₃)CF(OR)C₄F₉
CF₃OCF₂CF₂CF₂OCF(CF₃)CF(OR)CF(CF₃)OC₃F₇
CF₃OCF₂CF₂CF₂OCF(CF₃)CF(OR)CF₂CF₂OCF₃
CF₃OCF₂CF₂CF₂OCF(CF₃)CF(OR)CF₂CF₂H
CF₃OCF₂CF₂CF₂OCF(CF₃)CF(OR)CF₂CF₂OCH₃
CF₃OCF₂CF₂CF₂OCF(CF₃)CF(OR)CF(CF₃)OCF₂CF₂CF₂OCF₃

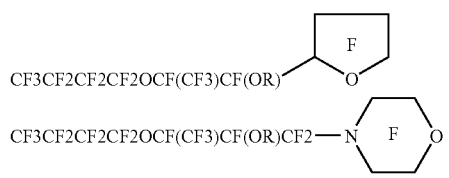

C₅F₁₁OCF(CF₃)CF(OR)CF₃, C₅F₁₁OCF(CF₃)CF(OR)CF₂CF₃ C₅F₁₁OCF(CF₃)CF(OR)CF₂CF₂CF₃, C₅F₁₁OCF(CF₃)CF(OR)CF(CF₃)₂ C₅F₁₁OCF(CF₃)CF(OR)C₄F₉, C₅F₁₁OCF(CF₃)CF(OR)CF(CF₃)OC₃F₇ C₅F₁₁OCF(CF₃)CF(OR)CF₂CF₂OCF₃, C₅F₁₁OCF(CF₃)CF(OR)CF₂CF₂H C₅F₁₁OCF(CF₃)CF(OR)CF₂CF₂OCH₃, C₅F₁₁OCF(CF₃)CF(OR)CF(CF₃)OC₄F₉

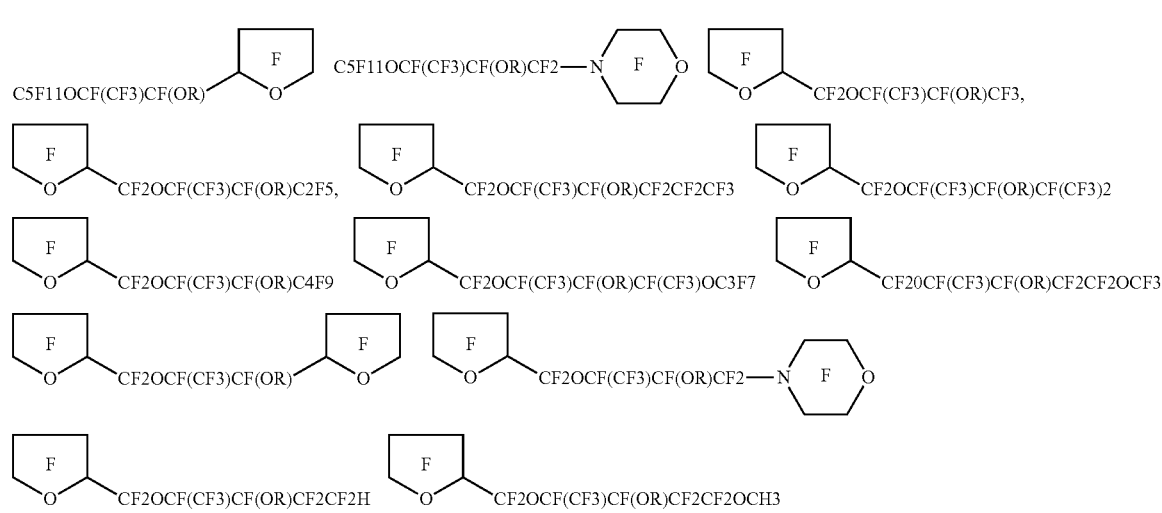

-continued

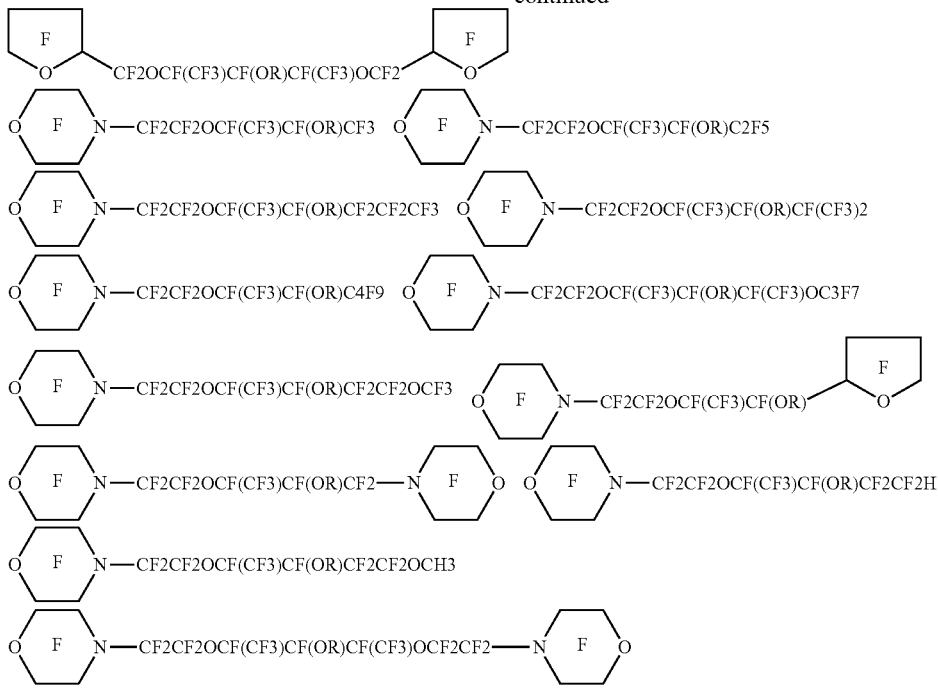

C$_3$F$_7$OCF(CF$_3$)CF$_2$OCF(CF$_3$)CF(OR)CF$_3$, C$_3$F$_7$OCF(CF$_3$)CF$_2$OCF(CF$_3$)CF(OR)C$_2$F$_5$, C$_3$F$_7$OCF(CF$_3$)CF$_2$OCF(CF$_3$)CF(OR)CF$_2$CF$_2$CF$_3$, C$_3$F$_7$OCF(CF$_3$)CF$_2$OCF(CF$_3$)CF(OR)CF(CF$_3$)$_2$, C$_3$F$_7$OCF(CF$_3$)CF$_2$OCF(CF$_3$)(CF$_3$)CF(OR)C$_4$F$_9$, C$_3$F$_7$OCF(CF$_3$)CF$_2$OCF(CF$_3$)CF(OR)CF(CF$_3$)OC$_3$F$_7$, C$_3$F$_7$OCF(CF$_3$)CF$_2$OCF(CF$_3$)CF(OR)CF$_2$CF$_2$OCF$_3$, C$_3$F$_7$OCF(CF$_3$)CF$_2$OCF(CF$_3$)CF(OR)CF$_2$CF$_2$H, C$_3$F$_7$OCF(CF$_3$)CF$_2$OCF(CF$_3$)CF(OR)CF$_2$CF$_2$OCH$_3$, C$_3$F$_7$OCF(CF$_3$)CF$_2$OCF(CF$_3$)CF(OR)CF(CF$_3$)OCF$_2$CF(CF$_3$)OC$_3$F$_7$

CH$_3$OCF$_2$CF$_2$CF$_2$OCF(CF$_3$)CF(OR)CF$_2$CF$_2$CF$_3$
CH$_3$OCF$_2$CF$_2$CF$_2$OCF(CF$_3$)CF(OR)CF(CF$_3$)$_2$
CH$_3$OCF$_2$CF$_2$CF$_2$OCF(CF$_3$)CF(OR)C$_4$F$_9$
CH$_3$OCF$_2$CF$_2$CF$_2$OCF(CF$_3$)CF(OR)CF(CF$_3$)OC$_3$F$_7$
CH$_3$OCF$_2$CF$_2$CF$_2$OCF(CF$_3$)CF(OR)CF$_2$CF$_2$OCF$_3$
CH$_3$OCF$_2$CF$_2$CF$_2$OCF(CF$_3$)CF(OR)CF$_2$CF$_2$H
CH$_3$OCF$_2$CF$_2$CF$_2$OCF(CF$_3$)CF(OR)CF$_2$CF$_2$OCH$_3$
CH$_3$OCF$_2$CF$_2$CF$_2$OCF(CF$_3$)CF(OR)CF(CF$_3$)OCF$_2$CF$_2$CF$_2$OCH$_3$

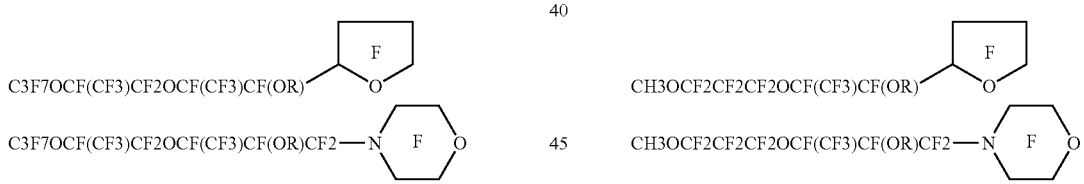

HCF$_2$CF$_2$CF$_2$OCF(CF$_3$)CF(OR)CF$_3$, HCF$_2$CF$_2$CF$_2$OCF(CF$_3$)CF(OR)CF$_2$CF$_3$, HCF$_2$CF$_2$CF$_2$OCF(CF$_3$)CF(OR)CF$_2$CF$_2$CF$_3$, HCF$_2$CF$_2$CF$_2$OCF(CF$_3$)CF(OR)CF(CF$_3$)$_2$, HCF$_2$CF$_2$CF$_2$OCF(CF$_3$)CF(OR)C$_4$F$_9$, HCF$_2$CF$_2$CF$_2$OCF(CF$_3$)CF(OR)CF(CF$_3$)OC$_3$F$_7$, HCF$_2$CF$_2$CF$_2$OCF(CF$_3$)CF(OR)CF$_2$CF$_2$OCF$_3$, HCF$_2$CF$_2$CF$_2$OCF(CF$_3$)CF(OR)CF$_2$CF$_2$H, HCF$_2$CF$_2$CF$_2$OCF(CF$_3$)CF(OR)CF$_2$CF$_2$OCH$_3$, HCF$_2$CF$_2$CF$_2$OCF(CF$_3$)CF(OR)CF(CF$_3$)OCF$_2$CF$_2$CF$_2$H and the like, and mixtures thereof.

Preferred hydrofluoroether compounds include the following, where R is selected from CH$_3$, C$_2$H$_5$, C$_3$H$_7$, and C$_4$H$_9$:
CF$_3$OCF(CF$_3$)CF(OR)CF$_3$, CF$_3$OCF(CF$_3$)CF(OR)C$_2$F$_5$, CF$_3$OCF(CF$_3$)CF(OR)CF$_2$CF$_2$CF$_3$, CF$_3$OCF(CF$_3$)CF(OR)CF(CF$_3$)$_2$, CF$_3$OCF(CF$_3$)CF(OR)C$_4$F$_9$, CF$_3$OCF(CF$_3$)CF(OR)CF$_3$)OCF$_3$ CF$_3$OCF(CF$_3$)CF(OR)CF(CF$_3$)OC$_3$F$_7$, CF$_3$OCF(CF$_3$)CF(OR)CF$_2$CF$_2$OCF$_3$

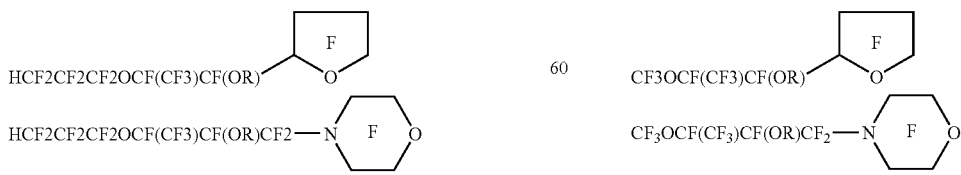

CH$_3$OCF$_2$CF$_2$CF$_2$OCF(CF$_3$)CF(OR)CF$_3$;
CH$_3$OCF$_2$CF$_2$CF$_2$OCF(CF$_3$)CF(OR)CF$_2$CF$_3$

C$_2$F$_5$OCF(CF$_3$)CF(OR)CF$_3$, C$_2$F$_5$OCF(CF$_3$)CF(OR)C$_2$F$_5$
C$_2$F$_5$OCF(CF$_3$)CF(OR)CF$_2$CF$_2$CF$_3$, C$_2$F$_5$OCF(CF$_3$)CF (OR)CF(CF$_3$)$_2$   C$_2$F$_5$OCF(CF$_3$)CF(OR)C$_4$F$_9$,   C$_2$F$_5$OCF
(CF$_3$)CF(OR)CF(CF$_3$)OC$_3$F$_7$   C$_2$F$_5$OCF(CF$_3$)CF(OR)
CF$_2$CF$_2$OCF$_3$, C$_2$F$_5$OCF(CF$_3$)CF(OR)CF(CF$_3$)OC$_2$F$_5$

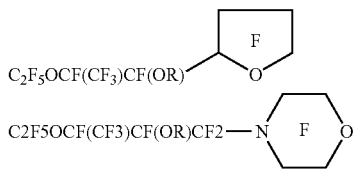

CF$_3$CF$_2$CF$_2$OCF(CF$_3$)CF(OR)CF$_3$,  CF$_3$CF$_2$CF$_2$OCF(CF$_3$)
CF(OR)C$_2$F$_5$   CF$_3$CF$_2$CF$_2$OCF(CF$_3$)CF(OR)CF$_2$CF$_2$CF$_3$,
CF$_3$CF$_2$CF$_2$OCF(CF$_3$)CF(OR)CF(CF$_3$)$_2$   CF$_3$CF$_2$CF$_2$OCF
(CF$_3$)CF(OR)C$_4$F$_9$, CF$_3$CF$_2$CF$_2$OCF(CF$_3$)CF(OR)CF(CF$_3$)
OC$_3$F$_7$ CF$_3$CF$_2$CF$_2$OCF(CF$_3$)CF(OR)CF$_2$CF$_2$OCF$_3$

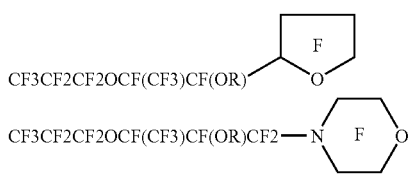

CF$_3$CF$_2$CF$_2$CF$_2$OCF(CF$_3$)CF(OR)CF$_3$,
CF$_3$CF$_2$CF$_2$CF$_2$OCF(CF$_3$)CF(OR)CF$_2$CF$_3$
CF$_3$CF$_2$CF$_2$CF$_2$OCF(CF$_3$)CF(OR)CF$_2$CF$_2$CF$_3$
CF$_3$CF$_2$CF$_2$CF$_2$OCF(CF$_3$)CF(OR)CF(CF$_3$)$_2$,
CF$_2$CF$_2$CF$_2$CF$_2$OCF(CF$_3$)CF(OR)C$_4$F$_9$
CF$_2$CF$_2$CF$_2$CF$_2$OCF(CF$_3$)CF(OR)CF(CF$_3$)OC$_3$F$_7$
CF$_2$CF$_2$CF$_2$CF$_2$OCF(CF$_3$)CF(OR)CF$_2$CF$_2$OCF$_3$
CF$_2$CF$_2$CF$_2$CF$_2$OCF(CF$_3$)CF(OR)CF(CF$_3$)OC$_4$F$_9$

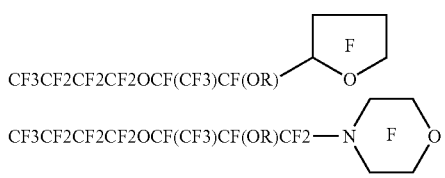

(CF$_3$)$_2$CFCF$_2$OCF(CF$_3$)CF(OR)CF$_3$,   (CF$_3$)$_2$CFCF$_2$OCF
(CF$_3$)CF(OR)CF$_2$CF$_3$   (CF$_3$)$_2$CFCF$_2$OCF(CF$_3$)CF(OR)
CF$_2$CF$_2$CF$_3$   (CF$_3$)$_2$CFCF$_2$OCF(CF$_3$)CF(OR)CF(CF$_3$)$_2$,
(CF$_3$)$_2$CFCF$_2$OCF(CF$_3$)CF(OR)C$_4$F$_9$   (CF$_3$)$_2$CFCF$_2$OCF
(CF$_3$)CF(OR)CF(CF$_3$)OC$_3$F$_7$   (CF$_3$)$_2$CFCF$_2$OCF(CF$_3$)CF
(OR)CF$_2$CF$_2$OCF$_3$   (CF$_3$)$_2$CFCF$_2$OCF(CF$_3$)CF(OR)CF
(CF$_3$)OC$_4$F$_9$

CF$_3$OCF$_2$CF$_2$CF$_2$OCF(CF$_3$)CF(OR)CF$_3$
CF$_3$OCF$_2$CF$_2$CF$_2$OCF(CF$_3$)CF(OR)CF$_2$CF$_3$
CF$_3$OCF$_2$CF$_2$CF$_2$OCF(CF$_3$)CF(OR)CF$_2$CF$_2$CF$_3$
CF$_3$OCF$_2$CF$_2$CF$_2$OCF(CF$_3$)CF(OR)CF(CF$_3$)$_2$
CF$_3$OCF$_2$CF$_2$CF$_2$OCF(CF$_3$)CF(OR)C$_4$F$_9$
CF$_3$OCF$_2$CF$_2$CF$_2$OCF(CF$_3$)CF(OR)CF(CF$_3$)OC$_3$F$_7$
CF$_3$OCF$_2$CF$_2$CF$_2$OCF(CF$_3$)CF(OR)CF$_2$CF$_2$OCF$_3$
CF$_3$OCF$_2$CF$_2$CF$_2$OCF(CF$_3$)CF(OR)CF(CF$_3$)
OCF$_2$CF$_2$CF$_2$OCF$_3$

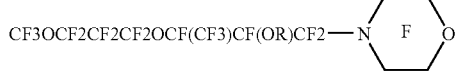

C$_5$F$_{11}$OCF(CF$_3$)CF(OR)CF$_3$,   C$_5$F$_{11}$OCF(CF$_3$)CF(OR)
CF$_2$CF$_3$  C$_5$F$_{11}$OCF(CF$_3$)CF(OR)CF$_2$CF$_2$CF$_3$, C$_5$F$_{11}$OCF
(CF$_3$)CF(OR)CF(CF$_3$)$_2$   C$_5$F$_{11}$OCF(CF$_3$)CF(OR)C$_4$F$_9$,
C$_5$F$_{11}$OCF(CF$_3$)CF(OR)CF(CF$_3$)OC$_3$F$_7$   C$_5$F$_{11}$OCF(CF$_3$)
CF(OR)CF$_2$CF$_2$OCF$_3$,   C$_5$F$_{11}$OCF(CF$_3$)CF(OR)CF(CF$_3$)
OC$_4$F$_9$

  

 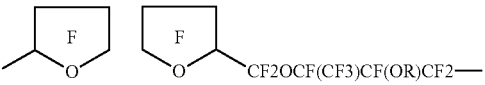 

 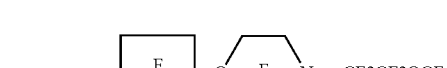 

 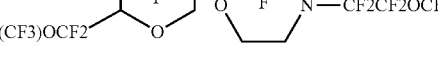 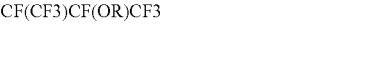

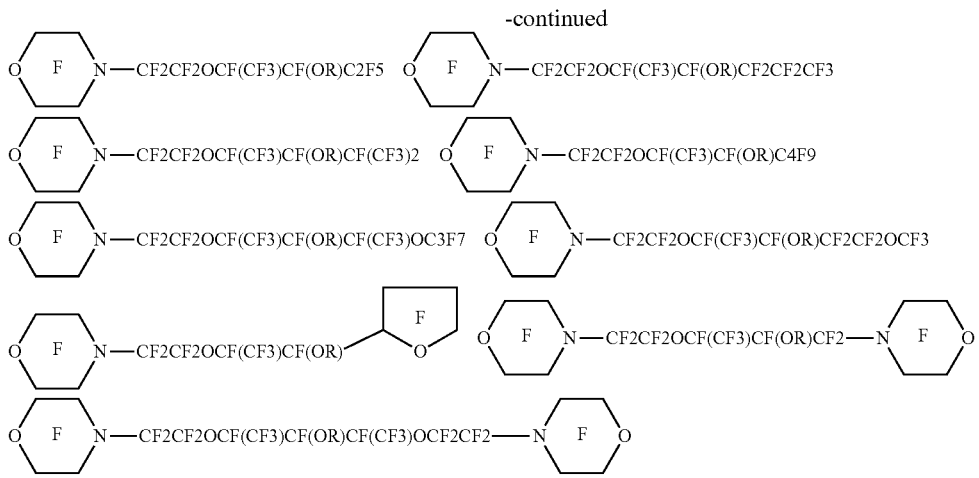

$C_3F_7OCF(CF_3)CF_2OCF(CF_3)CF(OR)CF_3$, $C_3F_7OCF(CF_3)CF_2OCF(CF_3)CF(OR)C_2F_5$, $C_3F_7OCF(CF_3)CF_2OCF(CF_3)CF(OR)CF_2CF_2CF_3$, $C_3F_7OCF(CF_3)CF_2OCF(CF_3)CF(OR)CF(CF_3)_2$, $C_3F_7OCF(CF_3)CF_2OCF(CF_3)(CF_3)CF(OR)C_4F_9$, $C_3F_7OCF(CF_3)CF_2OCF(CF_3)CF(OR)CF(CF_3)OC_3F_7$, $C_3F_7OCF(CF_3)CF_2OCF(CF_3)CF(OR)CF_2CF_2OCF_3$, $C_3F_7OCF(CF_3)CF_2OCF(CF_3)CF(OR)CF(CF_3)OCF_2CF(CF_3)OC_3F_7$

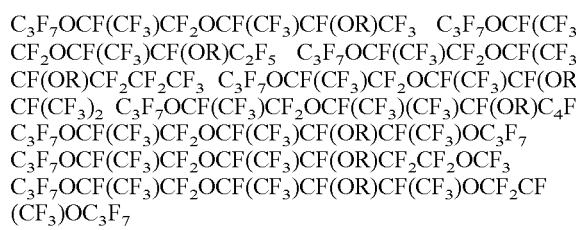

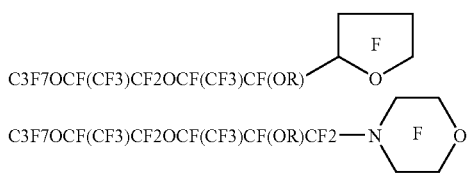

and mixtures thereof;
with more preferred compounds including the following, where R is selected from $CH_3$ and $C_2H_5$:
$CF_3OCF(CF_3)CF(OR)CF_3$, $CF_3OCF(CF_3)CF(OR)C_2F_5$, $CF_3OCF(CF_3)CF(OR)CF_2CF_2CF_3$, $CF_3OCF(CF_3)CF(OR)CF(CF_3)_2$ $CF_3OCF(CF_3)CF(OR)C_4F_9$, $CF_3OCF(CF_3)CF(OR)CF(CF_3)OCF_3$ $CF_3OCF(CF_3)CF(OR)CF(CF_3)OC_3F_7$, $CF_3OCF(CF_3)CF(OR)CF_2CF_2OCF_3$

$C_2F_5OCF(CF_3)CF(OR)CF_3$, $C_2F_5OCF(CF_3)CF(OR)C_2F_5$ $C_2F_5OCF(CF_3)CF(OR)CF_2CF_2CF_3$, $C_2F_5OCF(CF_3)CF(OR)CF(CF_3)_2$ $C_2F_5OCF(CF_3)CF(OR)C_4F_9$, $C_2F_5OCF(CF_3)CF(OR)CF(CF_3)OC_3F_7$ $C_2F_5OCF(CF_3)CF(OR)CF_2CF_2OCF_3$, $C_2F_5OCF(CF_3)CF(OR)CF(CF_3)OC_2F_5$

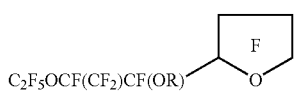

-continued

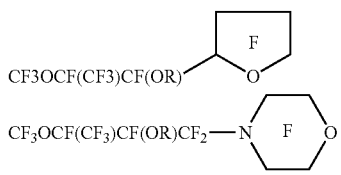

$CF_3CF_2CF_2OCF(CF_3)CF(OR)CF_3$, $CF_3CF_2CF_2OCF(CF_3)CF(OR)C_2F_5$ $CF_3CF_2CF_2OCF(CF_3)CF(OR)CF_2CF_2CF_3$, $CF_3CF_2CF_2OCF(CF_3)CF(OR)CF(CF_3)_2$ $CF_3CF_2CF_2OCF(CF_3)CF(OR)C_4F_9$, $CF_3CF_2CF_2OCF(CF_3)CF(OR)CF(CF_3)OC_3F_7$ $CF_3CF_2CF_2OCF(CF_3)CF(OR)CF_2CF_2OCF_3$

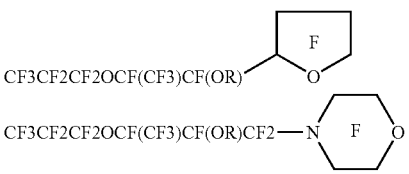

$CF_3CF_2CF_2CF_2OCF(CF_3)CF(OR)CF_3$,
$CF_3CF_2CF_2CF_2OCF(CF_3)CF(OR)CF_2CF_3$
$CF_3CF_2CF_2CF_2OCF(CF_3)CF(OR)CF_2CF_2CF_3$
$CF_3CF_2CF_2CF_2OCF(CF_3)CF(OR)CF(CF_3)_2$,
$CF_2CF_2CF_2CF_2OCF(CF_3)CF(OR)C_4F_9$
$CF_2CF_2CF_2CF_2OCF(CF_3)CF(OR)CF(CF_3)OC_3F_7$
$CF_2CF_2CF_2CF_2OCF(CF_3)CF(OR)CF_2CF_2OCF_3$
$CF_2CF_2CF_2CF_2OCF(CF_3)CF(OR)CF(CF_3)OC_4F_9$

$(CF_3)_2CFCF_2OCF(CF_3)CF(OR)CF_3$, $(CF_3)_2CFCF_2OCF(CF_3)CF(OR)CF_2CF_3$ $(CF_3)_2CFCF_2OCF(CF_3)CF(OR)CF_2CF_2CF_3$ $(CF_3)_2CFCF_2OCF(CF_3)CF(OR)CF(CF_3)_2$, $(CF_3)_2CFCF_2OCF(CF_3)CF(OR)C_4F_9$ $(CF_3)_2CFCF_2OCF(CF_3)CF(OR)CF(CF_3)OC_3F_7$ $(CF_3)_2CFCF_2OCF(CF_3)CF(OR)CF_2CF_2OCF_3$ $(CF_3)_2CFCF_2OCF(CF_3)CF(OR)CF(CF_3)OC_4F_9$

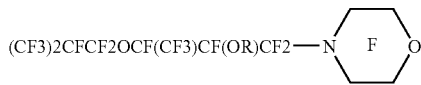
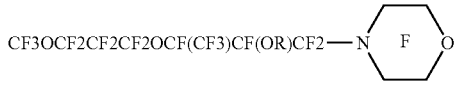
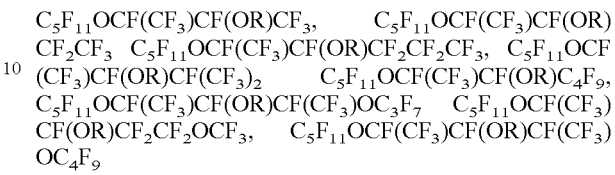
$C_5F_{11}OCF(CF_3)CF(OR)CF_3$, $C_5F_{11}OCF(CF_3)CF(OR)CF_2CF_3$  $C_5F_{11}OCF(CF_3)CF(OR)CF_2CF_2CF_3$, $C_5F_{11}OCF(CF_3)CF(OR)CF(CF_3)_2$  $C_5F_{11}OCF(CF_3)CF(OR)C_4F_9$, $C_5F_{11}OCF(CF_3)CF(OR)CF(CF_3)OC_3F_7$  $C_5F_{11}OCF(CF_3)CF(OR)CF_2CF_2OCF_3$, $C_5F_{11}OCF(CF_3)CF(OR)CF(CF_3)OC_4F_9$
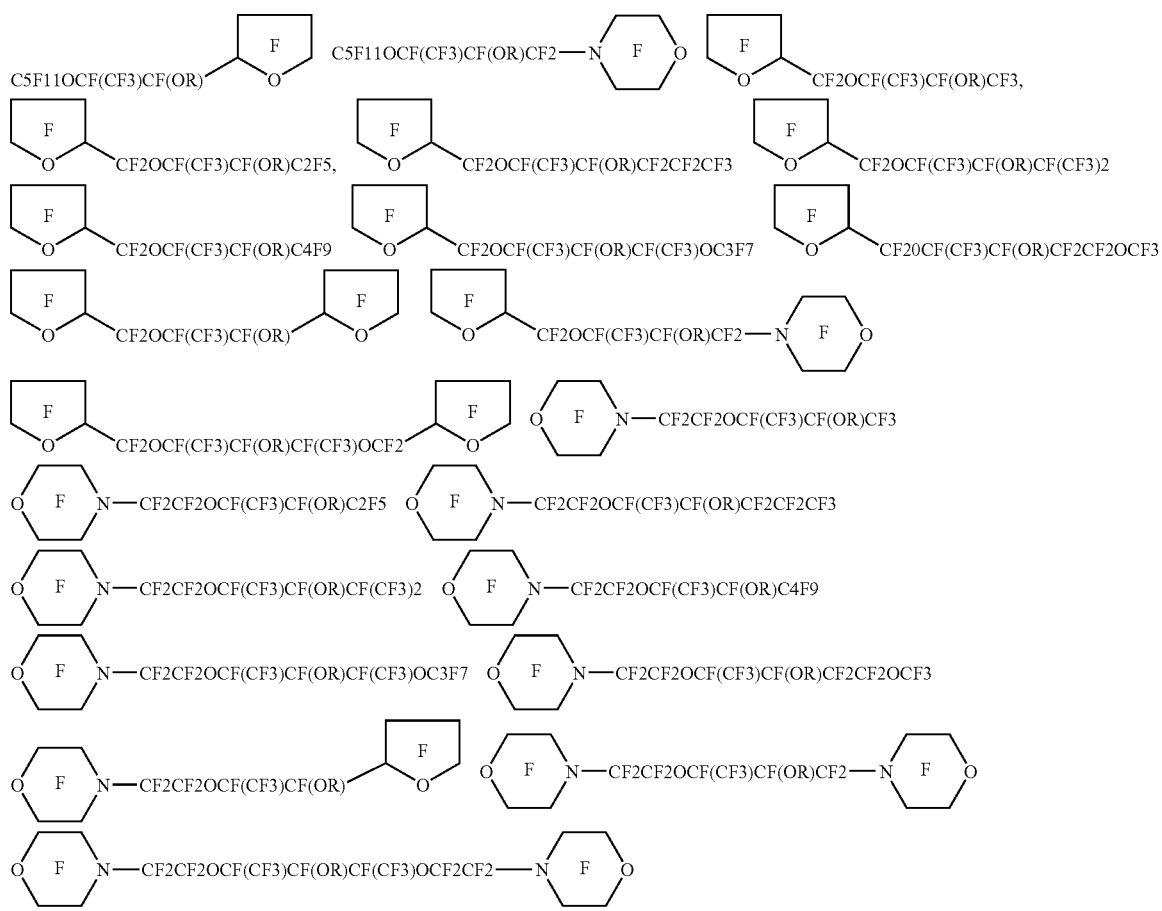
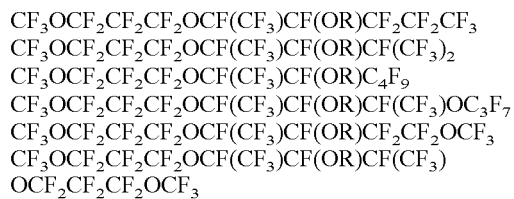
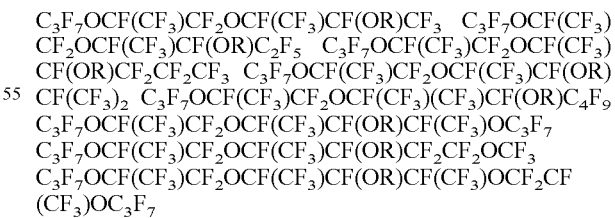
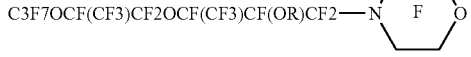
and mixtures thereof.

The hydrofluoroether compounds of the invention are hydrophobic and less oleophobic than their perfluoroether analogs, relatively chemically unreactive, thermally stable, water insoluble, and they can be made in accordance with this invention in high yield, high purity, and with a wide range of molecular weights. Their covalent carbon-hydrogen bonds are generally degradable by atmospheric photo-oxidation, thus making the hydrofluoroether compounds environmentally acceptable or compatible.

Preparation of Hydrofluoroether Compounds

The hydrofluoroether compounds (HFEs) of the invention can be prepared by the alkylation of fluorochemical alkoxides prepared by the reaction of a fluorochemical ketone (more specifically, a fluorochemical ketone comprising two terminal, independently fluoroalkyl or perfluoroalkyl groups and an intervening oxytetrafluoroethylidene moiety bonded through its central carbon atom to a carbonyl group, each of the terminal groups optionally comprising at least one catenated heteroatom) with an anhydrous alkali metal fluoride (for example, potassium fluoride or cesium fluoride) or anhydrous silver fluoride (preferably, in an anhydrous polar, aprotic solvent). See, for example, the preparative methods described in French Patent Publication No. 2,287,432 and German Patent Publication No. 1,294,949, as well as the method described in detail in U.S. Pat. No. 5,750,797 (Vitcak et al.), the description of which is incorporated herein by reference.

The fluorochemical ketones can be prepared from the corresponding fluorochemical acid fluorides by combining at least one fluorochemical acid fluoride with at least one fluoro- or perfluorovinyl ether (for example, $C_3F_7OCF=CF_2$) in the presence of at least one anhydrous fluoride source (for example, anhydrous potassium fluoride) and at least one anhydrous, polar, aprotic solvent (for example, diglyme (that is, diethylene glycol dimethyl ether or bis(2-methoxy)ethyl ether)). A phase transfer catalyst can be utilized, if desired.

For example, a fluorochemical acid fluoride, an anhydrous fluoride source (generally a catalytic amount), a solvent, and, optionally, a phase transfer catalyst (generally a catalytic amount) can be combined in any order in any suitable reactor (for example, a metal reactor; preferably, a pressure reactor), which can then be sealed and heated to a desired reaction temperature (for example, about 75° C.) under autogenous pressure. At least a stoichiometric amount (up to a stoichiometric excess of one hundred percent or more) of fluoro- and/or perfluorovinyl ether can then be added to the reactor (or can be added continuously or in portions), generally with stirring or agitation of the reactor contents and, preferably, with temperature control.

After completion of fluoro- and/or perfluorovinyl ether addition, or after the reaction has run to completion, the reactor can be cooled and vented and the contents purified by any suitable separation method. For example, the resulting reaction mixture can be filtered (for example, to remove the fluoride source), phase separated (for example, to remove the solvent and catalyst), washed with a washing solvent (for example, washed with acetone to remove residual solvent and catalyst), phase separated (for example, to remove the washing solvent), and subjected to rotary evaporation and/or distillation (for example, to remove any residual volatile materials and to purify the resulting fluorochemical ketone product).

The fluorochemical acid fluorides (used for preparing the fluorochemical ketones) can be prepared from, for example, the corresponding hydrocarbon acid fluorides or acid chlorides (the latter of which are commercially available) or certain lactones, anhydrides, or dimethyl esters by electrochemical fluorination in anhydrous hydrogen fluoride or by direct fluorination using elemental fluorine. Suitable fluorochemical acid fluorides include those having no hydrogen atoms bonded to the carbon atom adjacent to the carbonyl moiety. Representative examples of such fluorochemical acid fluorides include $CF_3C(O)F$, $CF_3CF_2C(O)F$, $CF_3CF_2CF_2C(O)F$, $(CF_3)_2CFC(O)F$, $C_4F_9C(O)F$, $CF_3OCF_2CF_2C(O)F$, $C_3F_7OCF(CF_3)C(O)F$, $HCF_2CF_2C(O)F$, $CH_3OCF_2CF_2C(O)F$,

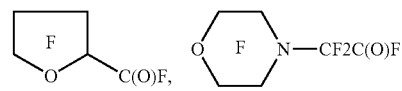

$CF_3CF_2OCF(CF3)C(O)F$, $C_3F_7OCF(CF_3)C(O)F$, $C_4F_9OCF(CF_3)C(O)F$, $C_5F_{11}OCF(CF_3)C(O)F$, $CF_3OCF_2CF_2CF_2OCF(CF_3)C(O)F$, $C_3F_7OCF(CF_3)CF_2OCF(CF_3)C(O)F$, $HCF_2CF_2CF_2OCF(CF_3)C(O)F$, $CH_3OCF_2CF_2CF_2OCF(CF_3)C(O)F$,

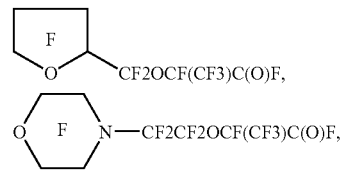

and the like, and mixtures thereof. Perfluorinated acid fluorides are generally preferred from a cost and availability perspective.

Fluoro- and perfluorovinyl ethers that are useful in carrying out the preparation process of the invention include those that possess a terminal perfluorovinyl group. Such fluoro- and perfluorovinyl ether starting compounds, which optionally can further contain one or more catenated heteroatoms (in addition to the ether oxygen of the fluoro- and perfluorovinyl ethers), can be prepared by the reaction of a fluorochemical acid fluoride or a fluorochemical ketone with hexafluoropropylene oxide (HFPO) to form an intermediate branched acid fluoride adduct. This adduct can then be reacted with a base to form an intermediate carboxylic acid salt, which can then be decarboxylated at elevated temperature (optionally, in the presence of an inert solvent). Some perfluorovinyl ethers (for example, perfluorovinyl ethers such as $C_3F_7OCF=CF_2$, $C_3F_7OCF(CF_3)CF_2OCF=CF_2$, and $CF_3OCF=CF_2$) are also commercially available (for example, from Synquest or from Apollo Scientific, Ltd.).

Representative examples of fluoro- and perfluorovinyl ethers that are useful in preparing the hydrofluoroether compounds include $C_3F_7OCF=CF_2$, $C_3F_7OCF(CF_3)CF_2OCF=CF_2$, $CF_3OCF=CF_2$, $C_4F_9OCF=CF_2$, $CF_3OC_3F_6OCF=CF_2$, $C_2F_5OCF=CF_2$, $(CF_3)_2CFCF_2OCF=CF_2$, $C_5F_{11}OCF=CF_2$, $HCF_2CF_2CF_2OCF=CF_2$, $CH_3OCF_2CF_2CF_2OCF=CF_2$, $CF_3CFHCF_2CF_2OCF=CF_2$,

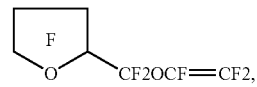

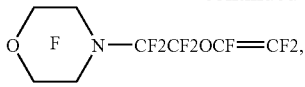

and the like, and mixtures thereof. Preferred vinyl ethers include $C_3F_7OCF=CF_2$, $C_4F_9OCF=CF_2$, $CF_3OC_3F_6OCF=CF_2$, $CF_3OCF=CF_2$, $C_3F_7OCF(CF_3)CF_2OCF=CF_2$, and mixtures thereof. $C_3F_7OCF=CF_2$, $C_4F_9OCF=CF_2$, and mixtures thereof are more preferred. (Mixtures of starting compounds can be used, if desired, but mixtures are generally less preferred due to the resulting production of product mixtures that can require purification.)

Suitable anhydrous fluoride sources include anhydrous fluorine-containing compounds that can dissociate to provide an anhydrous source of fluoride ion. Such compounds include metal fluorides (for example, potassium fluoride, rubidium fluoride, cesium fluoride, and the like, and mixtures thereof), metal bifluorides, quaternary ammonium fluorides, quaternary phophonium fluorides, and the like, and mixtures thereof. Preferred anhydrous fluoride sources include potassium fluoride, cesium fluoride, and mixtures thereof; with potassium fluoride being more preferred.

Suitable solvents include anhydrous, polar, aprotic solvents such as glycol ether solvents (for example, glyme, diglyme, triglyme, tetraglyme, and the like, and mixtures thereof), tetrahydrofuran, dimethylformamide, dimethyl sulfoxide, sulfolane, acetonitrile, and the like, and mixtures thereof. Preferred solvents include glyme, diglyme, triglyme, tetraglyme, dimethylformamide, and mixtures thereof; with glyme, diglyme, dimethylformamide, and mixtures thereof being more preferred and diglyme most preferred.

Suitable phase transfer catalysts include quaternary ammonium salts, quaternary phosphonium salts, crown ethers, cryptands, and the like, and mixtures thereof. Preferred salt counter ions include those that are commercially available (for example, chloride), as well as those such as monoalkyl sulfates, monoalkyl sulfonates, and the like, and mixtures thereof. Useful crown ethers include 4'-aminobenzyl-15-crown-5, 1-aza-12-crown-5, 1-aza-15-crown-5, 1-aza-18-crown-5, bis[(benzo-15-crown-5)-15-ylmethyl]pimelate, dicyclohexano-18-crown-6, 4'-formylbenzo-15-crown-5, 2-(hydroxymethyl)-15-crown-5, 4'-nitrobenzo-15-crown-5, poly[(dibenzo-18-crown-6)-coformaldehyde], and the like, and mixtures thereof. Useful commercially available cryptands include KRYPTOFIX 21, 211, 222, and 222b (available from Sigma-Aldrich Chemical Company, St. Louis, Mo.). Preferred catalysts are quaternary ammonium salts, due to their relative abundance and cost effectiveness. Useful commercially available quaternary ammonium salts include ADOGEN 464 (a methyltrialkyl($C_8$-$C_{10}$) ammonium chloride available from Sigma-Aldrich Chemical Company). Other preferred phase transfer catalysts are $(C_8H_{17})_3N^+CH_3^-OSO_3CH_3$, which can be prepared by reaction of trioctylamine with dimethylsulfate, and $(C_4H_9)_3N^+CH_3^-OSO_3CH_3$. If utilized, phase transfer catalyst is typically added at a concentration constituting between about 0.001 mol percent and about 5.0 mol percent of the reaction mixture.

In preparing the hydrofluoroether compounds of the invention, a fluorochemical ketone, an anhydrous fluoride source (generally a stoichiometric excess), an alkylating agent (generally a stoichiometric excess), a solvent, and, optionally, a phase transfer catalyst (generally a catalytic amount) can be combined in any order in any suitable reactor (for example, a metal reactor; preferably, a pressure reactor). The reactor can then be sealed and heated to a desired reaction temperature (for example, about 30-50° C.) under autogenous pressure for a period sufficient to achieve a desired level of conversion (for example, for about 16-72 hours), generally with stirring or agitation of the reactor contents and, preferably, with temperature control.

After the reaction has run to completion, the reactor can be cooled and vented and the contents purified by any suitable separation method. For example, the resulting reaction mixture can be filtered (for example, to remove the fluoride source), phase separated (for example, to remove the solvent and catalyst), washed with a washing solvent (for example, washed with acetone to remove residual solvent and catalyst), phase separated (for example, to remove the washing solvent), and subjected to rotary evaporation and/or distillation (for example, to remove any residual volatile materials and to purify the resulting HFE product).

Alternatively, after the reactor is cooled, the reactor contents can be treated with aqueous potassium hydroxide followed by an additional heating period (for example, 60° C. for about 1-3 hours) to react with and remove the excess alkylating agent. The resulting reaction mixture can then be purified as described above or, alternatively, can be subjected to steam distillation with separation of the resulting lower fluorochemical phase of the resulting distillate and further purification by, for example, fractional distillation.

Suitable (and preferred) anhydrous fluoride sources and phase transfer catalysts for use in preparing the hydrofluoroether compounds of the invention include those described above. Suitable fluorochemical ketone compounds include $CF_3OCF(CF_3)COCF_3$, $CF_3OCF(CF_3)COC_2F_5$ $CF_3OCF(CF_3)COCF_2CF_2CF_3$, $CF_3OCF(CF_3)COCF(CF_3)_2$ $CF_3OCF(CF_3)COC_4F_9$, $CF_3OCF(CF_3)COCF(CF_3)OCF_3$ $CF_3OCF(CF_3)COCF(CF_3)OC_3F_7$, $CF_3OCF(CF_3)COCF_2CF_2OCF_3$ $CF_3OCF(CF_3)COCF_2CF_2H$ $CF_3OCF(CF_3)COCF_2CF_2OCH_3$

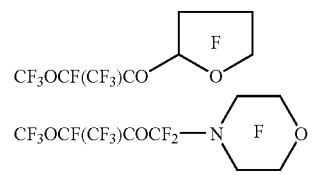

$C_2F_5OCF(CF_3)COCF_3$, $C_2F_5OCF(CF_3)COC_2F_5$ $C_2F_5OCF(CF_3)COCF_2CF_2CF_3$, $C_2F_5OCF(CF_3)COCF(CF_3)_2$ $C_2F_5OCF(CF_3)COC_4F_9$, $C_2F_5OCF(CF_3)COCF(CF_3)OC_3F_7$ $C_2F_5OCF(CF_3)COCF_2CF_2OCF_3$, $C_2F_5OCF(CF_3)COCF_2CF_2H$ $C_2F_5OCF(CF_3)COCF_2CF_2OCH_3$, $C_2F_5OCF(CF_3)COCF(CF_3)OC_2F_5$

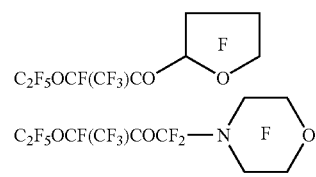

$CF_3CF_2CF_2OCF(CF_3)COCF_3$, $CF_3CF_2CF_2OCF(CF_3)COC_2F_5$ $CF_3CF_2CF_2OCF(CF_3)COCF_2CF_2CF_3$, $CF_3CF_2CF_2OCF(CF_3)COCF(CF_3)_2$ $CF_3CF_2CF_2OCF(CF_3)COC_4F_9$, $CF_3CF_2CF_2OCF(CF_3)COCF(CF_3)OC_3F_7$ $CF_3CF_2CF_2OCF(CF_3)COCF_2CF_2OCF_3$, $CF_3CF_2CF_2OCF(CF_3)COCF_2CF_2H$ $CF_3CF_2CF_2OCF(CF_3)COCF_2CF_2OCH_3$

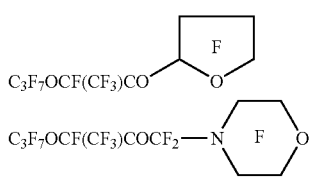

CF₃CF₂CF₂CF₂OCF(CF₃)COCF₃, CF₃CF₂CF₂CF₂OCF(CF₃)COCF₂CF₃ CF₃CF₂CF₂CF₂OCF(CF₃)COCF₂CF₂CF₃ CF₃CF₂CF₂CF₂OCF(CF₃)COCF(CF₃)₂, CF₂CF₂CF₂CF₂OCF(CF₃)COC₄F₉ CF₂CF₂CF₂CF₂OCF(CF₃)COCF(CF₃)OC₃F₇, CF₂CF₂CF₂CF₂OCF(CF₃)COCF₂CF₂OCF₃ CF₂CF₂CF₂CF₂OCF(CF₃)COCF₂CF₂H CF₂CF₂CF₂CF₂OCF(CF₃)COCF₂CF₂OCH₃ CF₂CF₂CF₂CF₂OCF(CF₃)COCF(CF₃)OC₄F₉

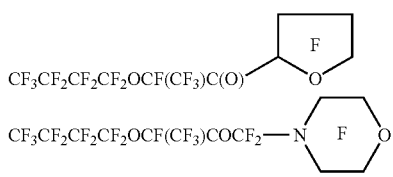

(CF₃)₂CFCF₂OCF(CF₃)COCF₃, (CF₃)₂CFCF₂OCF(CF₃)COCF₂CF₃ (CF₃)₂CFCF₂OCF(CF₃)COCF₂CF₂CF₃, (CF₃)₂CFCF₂OCF(CF₃)COCF(CF₃)₂, (CF₃)₂CFCF₂OCF(CF₃)COC₄F₉ (CF₃)₂CFCF₂OCF(CF₃)COCF(CF₃)OC₃F₇ (CF₃)₂CFCF₂OCF(CF₃)COCF₂CF₂OCF₃, (CF₃)₂CFCF₂OCF(CF₃)COCF₂CF₂H (CF₃)₂CFCF₂OCF(CF₃)COCF₂CF₂OCH₃ (CF₃)₂CFCF₂OCF(CF₃)COCF(CF₃)OC₄F₉

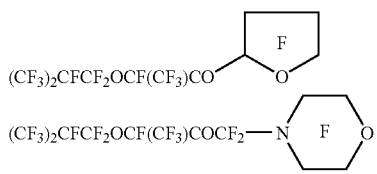

CF₃OCF₂CF₂CF₂OCF(CF₃)COCF₃ CF₃OCF₂CF₂CF₂OCF(CF₃)COCF₂CF₃ CF₃OCF₂CF₂CF₂OCF(CF₃)COCF₂CF₂CF₃ CF₃OCF₂CF₂CF₂OCF(CF₃)COCF(CF₃)₂ CF₃OCF₂CF₂CF₂OCF(CF₃)COC₄F₉ CF₃OCF₂CF₂CF₂OCF(CF₃)COCF(CF₃)OC₃F₇ CF₃OCF₂CF₂CF₂OCF(CF₃)COCF₂CF₂OCF₃ CF₃OCF₂CF₂CF₂OCF(CF₃)COCF₂CF₂H CF₃OCF₂CF₂CF₂OCF(CF₃)COCF₂CF₂OCH₃ CF₃OCF₂CF₂CF₂OCF(CF₃)COCF(CF₃)OCF₂CF₂CF₂OCF₃

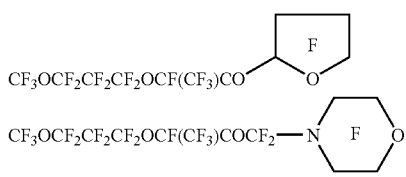

C₅F₁₁OCF(CF₃)COCF₃, C₅F₁₁OCF(CF₃)COCF₂CF₃ C₅F₁₁OCF(CF₃)COCF₂CF₂CF₃, C₅F₁₁OCF(CF₃)COCF(CF₃)₂ C₅F₁₁OCF(CF₃)COC₄F₉, C₅F₁₁OCF(CF₃)COCF(CF₃)OC₃F₇ C₅F₁₁OCF(CF₃)COCF₂CF₂OCF₃, C₅F₁₁OCF(CF₃)COCF₂CF₂H C₅F₁₁OCF(CF₃)COCF₂CF₂OCH₃, C₅F₁₁OCF(CF₃)COCF(CF₃)OC₄F₉

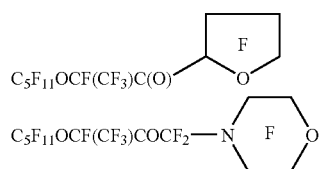
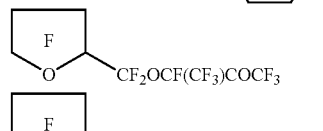
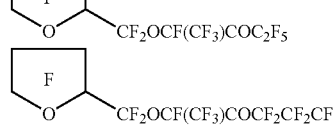
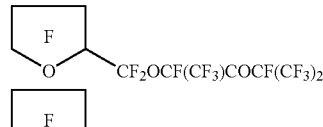
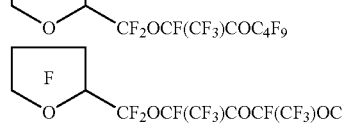
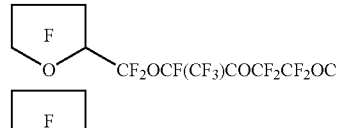
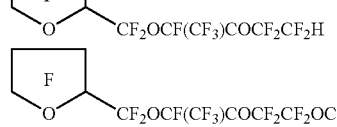
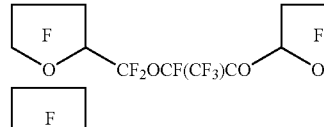
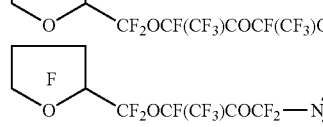
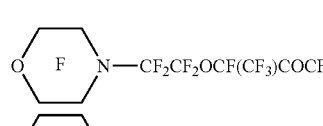
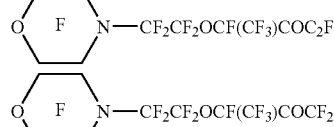
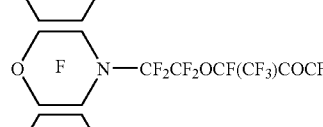
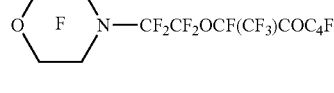

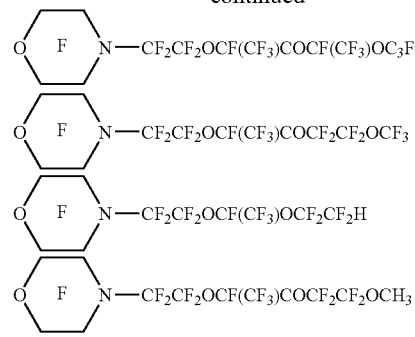
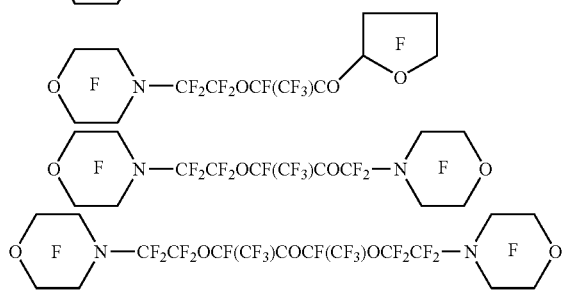
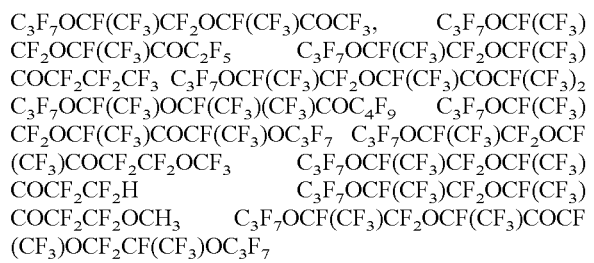
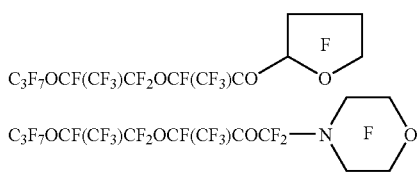
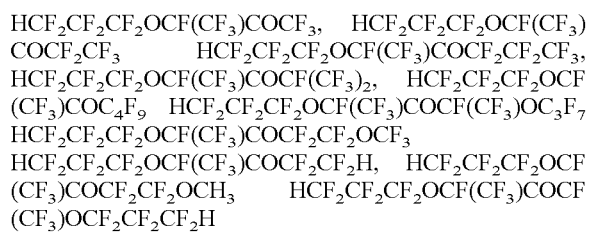

$C_3F_7OCF(CF_3)CF_2OCF(CF_3)COCF_3$, $C_3F_7OCF(CF_3)CF_2OCF(CF_3)COC_2F_5$ $C_3F_7OCF(CF_3)CF_2OCF(CF_3)COCF_2CF_2CF_3$ $C_3F_7OCF(CF_3)CF_2OCF(CF_3)COCF(CF_3)_2$ $C_3F_7OCF(CF_3)OCF(CF_3)(CF_3)COC_4F_9$ $C_3F_7OCF(CF_3)CF_2OCF(CF_3)COCF(CF_3)OC_3F_7$ $C_3F_7OCF(CF_3)CF_2OCF(CF_3)COCF_2CF_2OCF_3$ $C_3F_7OCF(CF_3)CF_2OCF(CF_3)COCF_2CF_2H$ $C_3F_7OCF(CF_3)CF_2OCF(CF_3)COCF_2CF_2OCH_3$ $C_3F_7OCF(CF_3)CF_2OCF(CF_3)COCF(CF_3)OCF_2CF(CF_3)OC_3F_7$

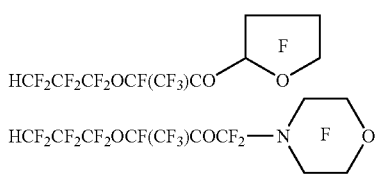

$HCF_2CF_2CF_2OCF(CF_3)COCF_3$, $HCF_2CF_2CF_2OCF(CF_3)COCF_2CF_3$ $HCF_2CF_2CF_2OCF(CF_3)COCF_2CF_2CF_3$, $HCF_2CF_2CF_2OCF(CF_3)COCF(CF_3)_2$, $HCF_2CF_2CF_2OCF(CF_3)COC_4F_9$ $HCF_2CF_2CF_2OCF(CF_3)COCF(CF_3)OC_3F_7$ $HCF_2CF_2CF_2OCF(CF_3)COCF_2CF_2OCF_3$ $HCF_2CF_2CF_2OCF(CF_3)COCF_2CF_2H$, $HCF_2CF_2CF_2OCF(CF_3)COCF_2CF_2OCH_3$ $HCF_2CF_2CF_2OCF(CF_3)COCF(CF_3)OCF_2CF_2CF_2H$

$CH_3OCF_2CF_2CF_2OCF(CF_3)COCF_3$, $CH_3OCF_2CF_2CF_2OCF(CF_3)COCF_2CF_3$ $CH_3OCF_2CF_2CF_2OCF(CF_3)COCF_2CF_2CF_3$ $CH_3OCF_2CF_2CF_2OCF(CF_3)COCF(CF_3)_2$ $CH_3OCF_2CF_2CF_2OCF(CF_3)COC_4F_9$ $CH_3OCF_2CF_2CF_2OCF(CF_3)COCF(CF_3)OC_3F_7$ $CH_3OCF_2CF_2CF_2OCF(CF_3)COCF_2CF_2OCF_3$ $CH_3OCF_2CF_2CF_2OCF(CF_3)COCF_2CF_2H$ $CH_3OCF_2CF_2CF_2OCF(CF_3)COCF_2CF_2OCH_3$ $CH_3OCF_2CF_2CF_2OCF(CF_3)COCF(CF_3)OCF_2CF_2CF_2OCH_3$

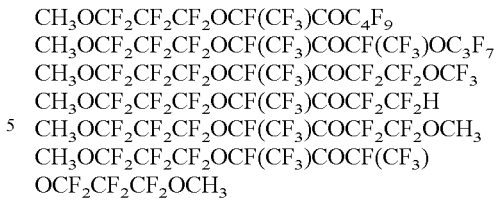
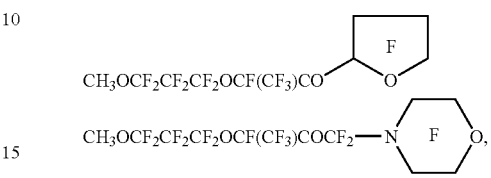

and the like, and mixtures thereof.

Suitable alkylating agents include dialkyl sulfates (for example, dimethyl sulfate); alkyl halides (for example, methyl iodide); alkyl p-toluenesulfonates (for example, methyl p-toluenesulfonate); alkyl perfluoroalkanesulfonates (for example, methyl perfluoromethanesulfonate); fluoroalkyl perfluoroalkanesulfonates (for example, 2,2,2-trifluoroethyl perfluorobutanesulfonate); difunctional alkylating agents including di-tosylates (for example, 1,3-propanediol di-p-toluenesulfonate), di-mesylates (for example, 1,4-butanediol bis(methanesulfonate)), and bis(perfluoroalkanesulfonates) (for example, 1,3-propanediol bis(nonafluorobutanesulfonate)); and the like; and mixtures thereof. Preferred alkylating agents include dialkyl sulfates and mixtures thereof.

Suitable (and preferred) polar, aprotic solvents include those described above, as well as acyclic ethers such as diethyl ether, ethylene glycol dimethyl ether, and diethylene glycol dimethyl ether; carboxylic acid esters such as methyl formate, ethyl formate, and methyl acetate; carbonate esters such as diethyl carbonate, propylene carbonate, and ethylene carbonate; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and the like; and mixtures thereof.

Use of Hydrofluoroether Compounds

The hydrofluoroether compounds of the invention (or a normally liquid composition comprising, consisting, or consisting essentially thereof) can be used in various applications. For example, the compounds can be used as solvents for precision or metal cleaning of electronic articles such as disks or circuit boards; as heat transfer agents (for example, for hybrid vehicle cooling and for the cooling or heating of integrated circuit tools in the semiconductor industry, including tools such as dry etchers, integrated circuit testers, photolithography exposure tools (steppers), ashers, chemical vapor deposition equipment, automated test equipment (probers), and physical vapor deposition equipment (sputterers)); as cell size regulators in making foam insulation (for example, polyurethane, phenolic, and thermoplastic foams); as carrier fluids or solvents for document preservation materials and for lubricants; as power cycle working fluids such as for heat pumps; as heat recovery fluids in Rankine cycle engines; as inert media for polymerization reactions; as buffing abrasive agents to remove buffing abrasive compounds from polished surfaces such as metal; as displacement drying agents for removing water, such as from jewelry or metal parts; as resist developers in conventional circuit manufacturing techniques including chlorine-type developing agents; and as strippers for photoresists when used with, for example, a chlorohydrocarbon such as 1,1,1-trichloroethane or trichloroethylene.

The hydrofluoroether compounds typically exhibit high dielectric strengths (for example, greater than about $10^8$ ohm-cm), which can make them well-suited for use in the semiconductor industry. The hydrofluoroether compounds that exhibit unexpectedly high thermal stabilities can be particularly useful in high temperature applications such as in heat transfer applications in the semiconductor industry and in flat screen panel manufacture, and the hydrofluoroether compounds that have boiling points above 100° C., as well as good low temperature viscosity characteristics, are particularly useful in applications that require cycling between high temperature and low temperature heat sinks.

The hydrofluoroether compounds can be used alone or in admixture with each other or with other commonly-used solvents (for example, alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, and the like, and mixtures thereof). Such co-solvents can be chosen to modify or enhance the properties of a composition for a particular use and can be utilized in ratios (of co-solvent(s) to hydrofluoroether(s)) such that the resulting composition preferably has no flash point. If desired, the hydrofluoroether compounds can be used in combination with other compounds that are very similar in properties relative to a particular use (for example, other hydrofluoroether compounds) to form compositions that "consist essentially" of the hydrofluoroether compounds of the invention.

Minor amounts of optional components can be added to the compounds to impart particular desired properties for particular uses. Useful compositions can comprise conventional additives such as, for example, surfactants, coloring agents, stabilizers, anti-oxidants, flame retardants, and the like, and mixtures thereof.

The hydrofluoroether compounds are useful as solvents for cleaning and drying applications such as, for example, those described in U.S. Pat. No. 5,125,089 (Flynn et al.), U.S. Pat. No. 3,903,012 (Brandreth), U.S. Pat. No. 4,169,807 (Zuber), and U.S. Pat. No. 5,925,611 (Flynn et al.), the descriptions of which are incorporated herein. Both organic and inorganic substrates can be cleaned by contacting them with a composition comprising at least one HFE of the invention. Most contaminants can be removed, including hydrocarbon contaminants, fluorocarbon contaminants, particulates, and water.

In using the compounds for the drying of or displacing water from the surface of articles (such as circuit boards), the process of drying or water displacement described in, for example, U.S. Pat. No. 5,125,978 (Flynn et al.) can be used. Broadly, such process comprises contacting the surface of an article with a liquid composition comprising at least one hydrofluoroether compound of the invention, preferably in admixture with a non-ionic fluoroaliphatic surface active agent. The wet article is immersed in the liquid composition and agitated therein, the displaced water is separated from the liquid composition, and the resulting water-free article is removed from the liquid composition. Further description of the process and the articles that can be treated can be found in said U.S. Pat. No. 5,125,978, which description is incorporated herein.

In using the compounds of the invention in vapor phase soldering, the process described in, for example, U.S. Pat. No. 5,104,034 (Hansen) can be used, which description is incorporated herein. Briefly, such process comprises immersing a component to be soldered in a body of vapor comprising at least one hydrofluoroether compound of this invention to melt the solder. In carrying out such a process, a liquid pool of a hydrofluoroether composition is heated to boiling in a tank to form a saturated vapor in the space between the boiling liquid and a condensing means, a workpiece to be soldered is immersed in the vapor whereby the vapor is condensed on the surface of the workpiece so as to melt and reflow the solder, and the soldered workpiece is then removed from the space containing the vapor.

In using the compounds of the invention as cell size regulators in making plastic foam (such as foamed polyurethane), the process reactants and reaction conditions described in, for example, U.S. Pat. No. 5,210,106 (Dams et al.) and U.S. Pat. No. 5,539,008 (Dams et al.) can be used, which descriptions are incorporated herein. One such process comprises vaporizing a blowing agent mixture in the presence of at least one foamable polymer or the precursors of at least one foamable polymer, the blowing agent mixture comprising at least one hydrofluoroether compound of the invention.

In using the compounds of the invention as heat transfer agents, the processes described in, for example, U.S. Reissue Pat. No. 37,119 E (Sherwood) and U.S. Pat. No. 6,374,907 B1 (Tousignant et al.) can be used, which descriptions are incorporated herein. In carrying out such processes, heat is transferred between a heat source (for example, a silicon wafer or a component of a flat panel display) and a heat sink through the use of a heat transfer agent comprising at least one hydrofluoroether compound of the invention. Unlike some HFEs that are used as heat transfer agents, the HFEs of the invention are not mixtures of components of widely disparate molecular weights. Rather, the HFEs are generally monodisperse (that is, of a single molecular weight). This means that their physical properties remain relatively constant over time, thereby avoiding significant heat transfer performance deterioration. In addition, the HFEs of the invention generally exhibit a wide liquid range, useful viscosity over that range, and relatively high thermal stability at end use temperatures, making them well-suited for use as heat transfer fluids.

In using the hydrofluoroether compounds of the invention as deposition solvents in coating applications or in document preservation applications, the processes described in, for example, U.S. Pat. No. 5,925,611 (Flynn et al.) and U.S. Pat. No. 6,080,448 (Leiner et al.) can be used, which descriptions are incorporated herein. Such processes for depositing a coating on a substrate (for example, magnetic recording media or cellulose-based materials) comprises applying, to at least a portion of at least one surface of the substrate, a composition comprising (a) a solvent composition comprising at least one hydrofluoroether compound of the invention; and (b) at least one coating material that is soluble or dispersible in the solvent composition. Coating materials that can be deposited by the process include pigments, lubricants, stabilizers, adhesives, anti-oxidants, dyes, polymers, pharmaceuticals, release agents, inorganic oxides, document preservation materials (for example, alkaline materials used in the deacidification of paper), and the like, and combinations thereof. Preferred materials include perfluoropolyether, hydrocarbon, and silicone lubricants; amorphous copolymers of tetrafluoroethylene; polytetrafluoroethylene; document preservation materials; and combinations thereof. Most preferably, the material is a perfluoropolyether lubricant or a document preservation material.

In using the hydrofluoroether compounds of the invention in cutting or abrasive working operations, the processes described in, for example, U.S. Pat. No. 6,759,374 (Milbrath et al.) can be used, the descriptions of which are incorporated herein. Such a process for metal, cermet, or composite working comprises applying a working fluid to a metal, cermet, or composite workpiece and tool, the working fluid comprising at least one hydrofluoroether compound of the invention and at least one lubricious additive. The working fluid can further comprise one or more conventional additives (for example, corrosion inhibitors, antioxidants, defoamers, dyes, bactericides, freezing point depressants, metal deactivators, co-solvents, and the like, and mixtures thereof).

In using the hydrofluoroether compounds of the invention as polymerization media or as chain transfer agents, the processes described in, for example, Research Disclosures, Number 40576, page 81 (January 1998) and in U.S. Pat. No. 5,182,342 (Feiring et al.) and U.S. Pat. No. 6,399,729 (Farnham et al.) can be used, the descriptions of which are incorporated herein. Such processes comprise polymerizing at least one monomer (preferably, at least one fluorine-containing monomer) in the presence of at least one polymerization initiator and at least one hydrofluoroether compound of the invention.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Sigma-Aldrich Chemical Company, St. Louis, Mo., unless otherwise noted.

In the following examples, mixtures of diastereomers were obtained due to the presence of two (or more) optical centers in the molecules. These diastereomers had boiling points that were very close together, and thus the diastereomers were not separated by distillation. In some cases, however, such diastereomers can be easily separated by gas chromatography.

Test Methods

Nuclear Magnetic Resonance (NMR)

$^1$H and $^{19}$F NMR spectra were run on a Varian UNITYplus 400 Fourier transform NMR spectrometer (available from Varian NMR Instruments, Palo Alto, Calif.).

Gas Chromatography/Mass Spectroscopy (GCMS)

GCMS samples were run on, for example, a Finnigan TSQ7000 mass spectrometer (available from Thermo Electron Corporation, Waltham, Mass.).

Gas Chromatography (GC)

GC samples were run on a Hewlett Packard 6890 Series Gas Chromatograph, obtainable from Agilent Technologies, Palo Alto, Calif.

Infrared (IR) Spectroscopy

IR spectra were run on a THERMO-NICOLET, Avatar 370 Fourier Transform Infrared (FTIR) Spectrometer (obtainable from Thermo Electron Corporation, Waltham, Mass.).

| Table of Abbreviations | |
|---|---|
| Abbreviation or Trade Designation | Description |
| b.p. | Boiling point, measured at ambient pressure unless otherwise specified |

Materials

Perfluoromorpholinoacetyl fluoride: Prepared by electrochemical fluorination (ECF) of methyl morpholinoacetate in a Simons ECF cell of essentially the type described in U.S. Pat. No. 2,713,593 (Brice et al.) and in R. E. Banks, *Preparation, Properties and Industrial Applications of Organofluorine Compounds*, pages 19-43, Halsted Press, New York (1982).

Potassium Fluoride: Obtained from Sigma-Aldrich Company, St. Louis, Mo. Spray-dried, stored in a 125° C. oven, and ground using mortar and pestle just before use.

Anhydrous Diglyme (anhydrous diethylene glycol dimethyl ether): Obtained from Sigma-Aldrich Company, St. Louis, Mo.

Methyltributylammonium methylsulfate: Prepared by reaction of dimethyl sulfate with tributylamine; 48.6 percent solution in diglyme.

Diethyl sulfate: Obtained from Sigma-Aldrich Company, St. Louis, Mo.

Perfluorobutyryl fluoride: Perfluorobutyryl fluoride, $CF_3CF_2CF_2COF$, was prepared by electrochemical fluorination of isobutyric anhydride. The gaseous products from the cell were further purified by two separate fractional distillations to obtain 98.5 percent perfluoro-n-butyryl fluoride. This material was used in subsequent reactions without further purification.

Adogen™ 464 phase transfer catalyst (methyltrialkyl ($C_8$-$C_{10}$) ammonium chloride, 49 percent (%) solution in anhydrous diglyme): Obtained from Sigma-Aldrich Company, St. Louis, Mo. Used typically as a diglyme solution containing Adogen™ 464, purified by fractional distillation to remove isopropyl alcohol.

Hexafluoropropene (HFP): Obtained from Dyneon, St. Paul, Minn.

Diethyl sulfate: Obtained from Sigma-Aldrich Company, St. Louis, Mo.

Dipropyl sulfate: Obtained from Sigma-Aldrich Company, St. Louis, Mo.

Potassium Hydroxide: Obtained from Sigma-Aldrich Company, St. Louis, Mo.

Magnesium Sulfate: Obtained from Sigma-Aldrich Company, St. Louis, Mo.

1,2-Dimethoxyethane: Obtained from Sigma-Aldrich Company, St. Louis, Mo.

Di-n-propylsulfate: Obtained from TCI America, Portland, Oreg.

1,3-Propanediol di-p-tosylate: Obtained from Sigma-Aldrich Company, St. Louis, Mo.

Dimethyl methyl succinate: Obtained from Sigma-Aldrich Company, St. Louis, Mo.

Novec™ HFE-7100 fluid (hydrofluoroether): Obtained from 3M Company, St. Paul, Minn.

Example 1

Preparation of

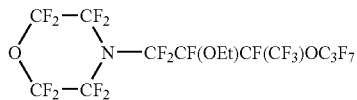

a—Preparation of Intermediate Ketone

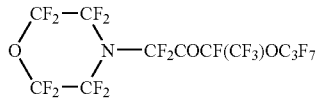

Perfluoromorpholinoacetyl fluoride (94.6 grams, 65 percent purity, 0.19 mole), $C_3F_7OCF=CF_2$ (50 grams, 0.19 mole), anhydrous diglyme (75 grams), potassium fluoride (2.2 grams, 0.04 mole, stored in a 125° C. oven and ground using a mortar and pestle just prior to use), and the phase transfer catalyst methyltributylammonium methylsulfate (1.2 grams of 48 percent solution in diglyme) were combined in a 600 mL Parr reaction vessel. The vessel was sealed, heated to 82° C. and held at that temperature for 16 hours. After cooling, the vessel was vented, the potassium fluoride solids were filtered, and the phases of the resulting two-phase reaction mixture were separated. The resulting ketone was purified by distillation (b.p.=145-146° C.) to 92 percent purity. IR spectra showed a CO absorbance at 1790.4 cm$^{-1}$.

b—Preparation of Ethyl Ether From Intermediate Ketone

The intermediate ketone from above (21.3 grams, 0.036 mole), anhydrous diglyme (100 grams), potassium fluoride (4.2 grams, 0.072 mole), methyltributylammonium methylsulfate (5.4 grams), and diethyl sulfate (11.0 grams, 0.072 mole) were combined in a 500 mL flask and heated with stirring to 52° C. for 16 hours. At the end of this time, potassium hydroxide (4.7 grams, dissolved in 75 grams water) was added, and the resulting mixture was distilled azeotropically using a Dean Stark trap, from which the resulting lower fluorochemical phase was separated during the distillation. The resulting product was distilled (b.p.=205° C., purity 92 percent). Its structure was confirmed by IR and GCMS.

Example 2

Preparation of $CF_3OC_3F_6OCF(CF_3)CF(OC_2H_5)CF(CF_3)OC_3F_7$ a—Preparation of Intermediate Ketone, $CF_3OC_3F_6OCF(CF_3)COCF(CF_3)OC_3F_7$ $CF_3OC_3F_6OCF(CF_3)COF$ (75 grams, 0.19 mole, prepared essentially as in Example 6a below, followed by reaction with hexafluoropropene oxide (HFPO) essentially as described in Example 5 below), $C_3F_7OCF=CF_2$ (50 grams, 0.19 mole), anhydrous diglyme (75 grams), potassium fluoride (2.2 grams, 0.04 mole), and the phase transfer catalyst methyltributylammonium methylsulfate (6.6 grams) were combined in a 600 mL Parr reaction vessel, and the vessel was sealed and heated to 75° C. for 16 hours. After cooling, the vessel was vented, the potassium fluoride solids were filtered, and the phases of the resulting two-phase reaction solution were separated. The resulting ketone was purified by distillation (b.p.=120-140° C. to 88 percent purity). IR spectra showed a CO absorbance at 1783.6 cm$^{-1}$.

b—Preparation of Ethyl Ether from Intermediate Ketone

The intermediate ketone from above (62.2 grams, 0.094 mole), anhydrous diglyme (150 mL), potassium fluoride (10.9 grams, 0.19 mole), methyltributylammonium methylsulfate (8.5 grams), and diethyl sulfate (28.9 grams, 0.19 mole) were combined in a 500 mL flask and heated with stirring to 52° C. for 16 hours. At the end of this time, potassium hydroxide (12.4 grams, dissolved in 75 grams of water) was added, and the resulting mixture was heated to 65° C. for about 45 minutes and then distilled azeotropically using a Dean Stark trap, from which the resulting lower fluorochemical phase was separated during the distillation. This provided 60.9 g of 70.9 percent purity by GC of two diastereomers, for a yield based on this GC data of 71 percent. The resulting product was distilled (b.p.=204° C.) to about 93 percent purity as a mixture of diastereomers. The structure of the product was confirmed by IR and GCMS.

Example 3

Preparation of $CF_3OC_3F_6OCF(CF_3)CF(OCH_3)CF(CF_3)OC_3F_7$

The ketone $CF_3OC_3F_6OCF(CF_3)COCF(CF_3)OC_3F_7$ (24.8 grams, 0.037 mole, prepared essentially as in Example 2 above), anhydrous diglyme (75 mL), potassium fluoride (4.3 grams, 0.075 mole), methyltributylammonium methylsulfate (6.5 grams), and dimethyl sulfate (10.4 grams, 0.082 mole) were combined in a 500 mL flask and heated with stirring to 32° C. for 16 hours. At the end of this time, potassium hydroxide (5.4 grams, dissolved in 75 grams water) was added, and the mixture was heated to 65° C. for about 45 minutes and then distilled azeotropically using a Dean Stark trap, from which the resulting lower fluorochemical phase was separated during the distillation. The resulting product was distilled (b.p.=196° C.) to a purity of about 95 percent as a mixture of diastereomers. The structure of the product was confirmed by IR and GCMS.

Example 4

Preparation of $C_3F_7OCF(CF_3)CF(OC_3H_7)C_3F_7$ a—Preparation of Intermediate Ketone, $C_3F_7OCF(CF_3)COC_3F_7$ n-$C_3F_7COF$ (56.1 grams, 0.26 mole), $C_3F_7OCF=CF_2$ (69.1 grams, 0.26 mole), anhydrous diglyme (75 grams), potassium fluoride (3.0 grams, 0.05 mole), and the phase transfer catalyst methyltributylammonium methylsulfate (1.7 grams) were combined in a 600 mL Parr reaction vessel, and the vessel was sealed and heated to 75° C. for 16 hours. After cooling, the vessel was vented, the potassium fluoride solids were filtered, and the phases of the resulting two-phase reaction solution were separated. The resulting product ketone was purified by distillation of lower boiling impurities to a purity of 95 percent. IR spectra showed a CO absorbance at 1784.7 cm$^{-1}$.

b—Preparation of Propyl Ether from Intermediate Ketone

The intermediate ketone $C_3F_7OCF(CF_3)COC_3F_7$ (35 grams, 0.074 mole), anhydrous diglyme (150 mL), potassium fluoride (8.4 grams, 0.15 mole), methyltributylammonium methylsulfate (5.4 grams), and dipropyl sulfate (26.4 grams, 0.15 mole) were combined in a 500 mL flask and heated with stirring to 52° C. for 16 hours. At the end of this time, potassium hydroxide (9.6 grams, dissolved in 100 grams water) was added, and the resulting mixture was heated to 65° C. for about 45 minutes and then distilled azeotropically using a Dean Stark trap, from which the resulting lower fluorochemical phase was separated during the distillation. The resulting product was distilled (b.p.=173-175° C.) to a purity of about 96 percent as a mixture of diastereomers. The structure of the product was confirmed by IR and GCMS.

Example 5

Preparation of 1,1,1,2,3,4,4,5,5,6,6,6-dodecafluoro-2-perfluorobutoxy-3-ethoxy hexane, $CF_3CF_2CF_2CF_2OCF(CF_3)CF(OCH_2CH_3)$ $CF_2CF_2CF_3$ a—Preparation of 1,1,1,2-tetrafluoro-2-perfluorobutoxy propionyl fluoride, $CF_3CF_2CF_2CF_2OCF(CF_3)C(O)F$ A clean, dry, 600 mL, stainless steel, Parr pressure reactor was charged with spray-dried potassium fluoride (6.0 grams, 0.10 mole) and anhydrous diglyme (100 grams). The reactor was sealed and cooled with a dry ice-acetone bath, charged with perfluorobutyryl fluoride (345 grams, 1.57 mole), and warmed to −7° C. with agitation. Hexafluoropropene oxide (308.7 grams, 1.86 mole) was added steadily over a 25 hour period, holding the temperature between −7° C. and −20° C. The resulting mixture was allowed to warm to room temperature and was vented to atmospheric pressure, and the resulting two-phase mixture was separated. The resulting lower fluorochemical phase was analyzed and found to contain 76 percent product acyl fluoride after conversion to the methyl ester by the addition of methanol. The crude 1,1,1,2-tetrafluoro-2-perfluorobutoxy propionyl fluoride was purified using a 10 perforated plate internal bellows column to provide 320 grams of product with 98.7 percent purity.

b—Preparation of perfluorobutyl trifluorovinyl ether, $CF_3CF_2CF_2CF_2OCF=CF_2$ A 500 mL, round bottom, single neck, flask with thermometer well was equipped with a magnetic stirrer, a heating mantle, thermocouple temperature readouts for both flask and column top temperatures, a 10 perforated plate silver coated vacuum jacketed distillation column with liquid phase head splitter, a water cooled condenser, and a nitrogen bubbler. The flask was charged with sodium carbonate (47 grams, 0.44 mole, stored in a 125° C. oven) and anhydrous diglyme (207 grams). This system was dried by distilling 95 grams of diglyme using a 7-1 reflux ratio and a final column top temperature of 158° C. The flask was cooled to ambient conditions, and 1,1,1,2-tetrafluoro-2-perfluorobutoxy propionyl fluoride (96.9 grams, 0.25 mole) was charged to the flask. The flask was slowly heated, and the resulting distillate was collected up to a column top temperature of 150° C. The distilled 73.9 grams of crude material contained 88.7 percent desired perfluorobutyl trifluorovinyl ether, as determined by GC.

c—Preparation of 1,1,1,2,3,4,4,5,5,6,6,6-dodecafluoro-2-perfluorobutoxy-3-ethoxy hexane in one reaction vessel A clean, dry, 600 mL, stainless steel, Parr pressure reactor was charged with spray-dried potassium fluoride (5.0 grams, 0.086 mole), anhydrous diglyme (100 grams), tributylmethylammonium methylsulfate (11.0 grams, 0.017 mole), and perfluorobutyl trifluorovinyl ether (73.9 grams, 0.207 mole). The reactor was sealed, cooled with a dry ice-acetone bath, and charged with perfluorobutyryl fluoride (81.0 grams, 0.367 mole). The reactor was then heated to 85° C. and held for 24 hours with agitation. The reactor was cooled to below 0° C. with a dry ice-acetone bath, vented, its agitation stopped, opened, and then immediately charged with spray-dried potassium fluoride (26.0 grams, 0.45 mole, stored in a 125° C. oven and ground using a mortar and pestle just prior to use) and diethyl sulfate (78.0 grams, 0.51 mole). The reactor was then sealed, heated to 52° C. with agitation, and held for 24 hours. Water (50 grams) and 45 percent KOH (80 grams, 0.64 mole) were added to the reactor using a 150 mL cylinder charge bomb containing these charges and pressurized to 6.8 atmospheres (100 psig) with nitrogen to facilitate the transfer. The reactor was heated to 65° C. and held for 4 hours to neutralize excess diethyl sulfate. The resulting crude product was isolated by steam distillation and washed one time with an equal weight of water to obtain 153.4 grams of product with a purity of 69.4 percent as determined by GC analysis. Purification to 99.8 percent was achieved by fractional distillation at atmospheric pressure using a concentric tube column. Product structure was confirmed by GCMS and $^{19}$F NMR.

Example 6

Preparation of 3-Ethoxy-1,1,1,2,3,4,4,5,5-nonafluoro-2-nonafluorobutyloxy-5-trifluoromethoxy-pentane, $CF_3CF_2CF_2CF_2OCF(CF_3)CF(OCH_2CH_3)$ $CF_2CF_2OCF_3$ a—Preparation of 3-Trifluoromethoxytetrafluoropropionyl fluoride, $CF_3OCF_2CF_2COF$ 3-Trifluoromethoxy tetrafluoropropionyl fluoride was prepared by electrochemical fluorination of methyl-3-methoxy-2,2,3,3-tetrafluoropropionate, $CH_3OCF_2CF_2CO_2CH_3$. The gaseous products from the cell were further purified by fractional distillation to obtain essentially 100 percent pure 3-trifluoromethoxy tetrafluoropropionyl fluoride. This material was used in subsequent reactions without further purification. As used herein, the term "3-trifluoromethoxy tetrafluoropropionyl fluoride" refers to this material.

b—Preparation of Ethyl Ether Product

A clean, dry, 600 mL, stainless steel, Parr pressure reactor was charged with spray-dried potassium fluoride (4.7 grams, 0.081 mole), anhydrous diglyme (228 grams), tributylmethylammonium methylsulfate (10.5 grams, 0.016 mole), cesium fluoride (0.6 grams, 0.004 mole), and perfluorobutoxy trifluorovinyl ether (prepared essentially as in Example 5, 130.6 grams, 0.333 mole). The reactor was sealed, cooled with a dry ice-acetone bath, charged with 3-trifluoromethoxy tetrafluoropropionyl fluoride (97.4 grams, 0.42 mole), heated to 87° C., and held for 27 hours with agitation. The reactor was cooled to below 0° C. with a dry ice-acetone bath, vented, its agitation stopped, opened, and then immediately charged with spray-dried potassium fluoride (24.8 grams, 0.43 mole) and diethyl sulfate (89.2 grams, 0.580 mole). The reactor was sealed, heated to 52° C. with agitation, and held for 65 hours. Water (50 grams) and 45 percent KOH (80 grams, 0.64 mole) were added to the reactor using a 150 mL cylinder charge bomb. The reactor was heated to 65° C. and held for 4 hours to neutralize excess diethyl sulfate. The resulting crude product was isolated by steam distillation and washed two times with equal weights of water to obtain 227.3 grams of product with a purity of 75.2 percent as determined by GC analysis. Purification to 99.8 percent was achieved by fractional distillation at atmospheric pressure using a concentric tube column. Product structure was confirmed by GCMS and $^{19}$F NMR.

Example 7

Preparation of 3-Ethoxy-1,1,1,2,3,4,4,5,5,6,6,6-dodecafluoro-2-(1,1,2,2,3,3-hexafluoro-3-trifluoromethoxypropoxy)hexane, $CF_3OCF_2CF_2CF_2OCF(CF_3)CF(OCH_2CH_3)CF_2CF_2CF_3$ A clean, dry, 600 mL, stainless steel, Parr pressure reactor was charged with spray-dried potassium fluoride (4.4 grams, 0.076 mole), anhydrous diglyme (208 grams), tributylmethylammonium methylsulfate (10 grams, 0.016 mole), and 3-trifluoromethoxy-1,1,2,2,3,3-hexafluoropropyl trifluorovinyl ether (118.9 grams, 0.33 mole). The reactor was sealed, cooled with a dry ice-acetone bath, charged with perfluorobutyryl fluoride (87.7 grams, 0.40 mole), heated to 87° C., and held for 40 hours with agitation. The reactor was cooled to ambient conditions, vented, its agitation stopped, opened, and then immediately charged with spray-dried potassium fluoride (23.6 grams, 0.406 mole) and diethyl sulfate (84.9 grams, 0.551 mole). The reactor was sealed, heated to 52° C. with agitation, and held for 20 hours. Water (50 grams) and 45 percent KOH (80 grams, 0.64 mole) were added to the reactor using a 150 mL cylinder charge bomb. The reactor was heated to 65° C. and held for 4 hours to neutralize excess diethyl sulfate. The resulting crude product was isolated by steam distillation and washed one time with an equal weight of water to obtain 183 grams of product with a purity of 72.1 percent as determined by GC analysis. Purification to greater than 99 percent was achieved by fractional distillation at atmospheric pressure using a concentric tube column. Product structure was confirmed by GCMS and $^{19}$F NMR.

Example 8

Preparation of 2-[(2-Ethoxy-1,2,3,3,4,4,4-heptafluoro-1-trifluoromethyl-butoxy)-difluoro-methyl]-2,3,3,4,4,5,5-heptafluorotetrahydrofuran, c-($C_4F_8O$)$CF_2OCF(CF_3)CF(OC_2H_5)CF_2CF_3$ a—Preparation of perfluorotetrahydro-2-furoyl fluoride, c-($C_4F_8O$)COF Perfluorotetrahydro-2-furoyl fluoride was prepared by electrochemical fluorination of 2-furoyl chloride. The gaseous products from the cell were further purified by fractional distillations to obtain 95 percent perfluorotetrahydro-2-furoyl fluoride. This material was used in subsequent reactions without further purification. As used herein, the term "perfluorotetrahydro-2-furoyl fluoride" refers to this material.

b—Preparation of perfluoropropionyl fluoride, $CF_3CF_2COF$

Perfluoropropionyl fluoride was prepared by electrochemical fluorination of propionic anhydride. The gaseous products from the cell were further purified by fractional distillations to obtain essentially 100 percent pure perfluoropropionyl fluoride. This material was used in subsequent reactions without further purification. As used herein, the term "perfluoropropionyl fluoride" refers to this material.

c—Preparation of 2-[Difluoro-(2,3,3,4,4,5,5-heptafluorotetrahydrofuran-2-yl)-methoxy]-2,3,3,3-tetrafluoro-propionyl fluoride, c-($C_4F_8O$)$CF_2OCF(CF_3)$COF A clean, dry, 600 mL, stainless steel, Parr pressure reactor was charged with spray-dried potassium fluoride (6.3 grams, 0.11 mole), cesium fluoride (1.0 gram, 0.007 mole), and anhydrous diglyme (52.5 grams). The reactor was sealed and cooled with a dry ice-acetone bath, charged with perfluorotetrahydro-2-furoyl fluoride (158.6 grams, 0.62 mole), and held at −20° C. with agitation. Hexafluoropropene oxide (106 grams, 0.64 mole) was added steadily over an 8 hour period, holding the temperature between 0° C. and −20° C. The resulting mixture was allowed to warm to room temperature, and 259 grams of 80.4 percent desired material was recovered by one-plate distillation.

d—Preparation of 2-(Perfluorotetrahydrofuryl)trifluorovinyl ether, c-($C_4F_8O$)$CF_2OCF{=}CF_2$ A 1 L, round bottom, single neck, flask with thermometer well was equipped with a magnetic stirrer, a heating mantle, thermocouple temperature readouts for both the flask and column top temperatures, a 10 perforated plate silver coated vacuum jacketed distillation column with liquid phase head splitter, a water cooled condenser, and a nitrogen bubbler. The flask was charged with sodium carbonate (107 grams, 1.01 mole, stored in a 125° C. oven) and anhydrous diglyme (500 grams). This system was dried by distilling 250 grams of diglyme using a 7-1 reflux ratio. The flask was cooled to ambient conditions, and 2-[difluoro-(2,3,3,4,4,5,5-heptafluorotetrahydrofuran-2-yl)-methoxy]-2,3,3,3-tetrafluoropropionyl fluoride (259 grams, 0.485 mole) was charged to the flask. The flask was slowly heated while collecting distillate up to a column top temperature of 150° C. The resulting 173.2 grams of crude product contained 77.0 percent desired product, as determined by GC.

e—Preparation of Ethyl Ether Product

A clean, dry, 600 mL, stainless steel, Parr pressure reactor was charged with spray-dried potassium fluoride (4.8 grams, 0.083 mole), anhydrous diglyme (225 grams), tributylmethylammonium methylsulfate (10.8 grams, 0.017 mole), and 2-perfluorotetrahydrofuryl trifluorovinyl ether (148.8 grams, 0.33 mole). The reactor was sealed, cooled with a dry ice-acetone bath, charged with perfluoropropionyl fluoride (80.5 grams, 0.485 mole), heated to 87° C., and held for 23 hours with agitation. The reactor was cooled to ambient conditions, vented, its agitation stopped, opened, and then immediately charged with spray-dried potassium fluoride (29.1 grams, 0.500 mole) and diethyl sulfate (98.8 grams, 0.641 mole). The reactor was sealed, heated to 52° C. with agitation, and held for 65 hours. Water (50 grams) and 45 percent KOH (80 grams, 0.64 mole) were added to the reactor using a 150 mL cylinder charge bomb. The reactor was heated to 65° C. and held for 4 hours to neutralize excess diethyl sulfate. The resulting crude product was isolated by steam distillation and washed one time with an equal weight of water to obtain 209.7 grams of crude product with a purity of 77.9 percent as determined by GC analysis. Purification to 99.0 percent was achieved by atmospheric fractional distillation using a concentric tube column. Product structure was confirmed by GCMS and $^{19}F$ NMR.

Example 9

Preparation of 1,1,1,2,3,4,4,5,5,5-Decafluoro-2-perfluorobutoxy-3-propoxy pentane
$CF_3CF_2CF_2CF_2OCF(CF_3)CF(OCH_2CH_2CH_3)$
$CF_2CF_3$ A clean, dry, 600 mL, stainless steel, Parr pressure reactor was charged with spray-dried potassium fluoride (3.3 grams, 0.057 mole), anhydrous diglyme (142 grams), tributylmethylammonium methylsulfate (7.4 grams, 0.012 mole), and perfluorobutyl trifluorovinyl ether (92 grams, 0.234 mole). The reactor was sealed, cooled with a dry ice-acetone bath, charged with perfluoropropionyl fluoride (49.0 grams, 0.30 mole), heated to 87° C., and held for 50 hours with agitation. The reactor was cooled to below −30° C. with a dry ice-acetone bath, vented, its agitation stopped, opened, and then immediately charged with spray-dried potassium fluoride (17.4 grams, 0.299 mole) and dipropyl sulfate (74.1 grams, 0.41 mole). The reactor was sealed, heated to 52° C. with agitation, and held for 48 hours. Water (50 grams) and 45 percent KOH (80 grams, 0.64 mole) were added to the reactor using a 150 mL cylinder charge bomb. The reactor was heated to 65° C. and held for 4 hours to neutralize excess diethyl sulfate. The resulting crude product was isolated by steam distillation and washed one time with an equal weight of water to provide 123.7 grams product with a purity of 70 percent as determined by GC analysis. Purification to 96 percent was achieved by atmospheric fractional distillation using a concentric tube column. Product structure was confirmed by GCMS and $^{19}F$ NMR.

Example 10

Preparation of $C_3F_7OCF(CF_3)CF_2OCF(CF_3)CF$
$(OC_2H_5)C_2F_5$

A clean, dry, 600 mL, stainless steel, Parr pressure reactor was charged with spray-dried potassium fluoride (10.0 grams, 0.17 mole), anhydrous diglyme (129 grams), and Adogen™ 464 phase transfer catalyst (2.2 grams). The reactor was sealed, cooled with a dry ice-acetone bath, evacuated, and charged with perfluoropropionyl fluoride (70.0 grams, 0.42 mole) and $C_3F_7OCF(CF_3)CF_2OCF=CF_2$ (170 grams, 0.39 mole). The reactor was heated to 85° C., held for 16 hours with agitation, and cooled to room temperature. The resulting intermediate ketone-containing reaction mixture (0.39 mole based on starting vinyl ether) was used without further purification and was combined with an additional amount of anhydrous diglyme (1000 grams), potassium fluoride (35.7 grams, 0.62 mole), catalyst (28 grams, 56 percent solution in diglyme), and diethyl sulfate (121.2 grams, 0.79 mole) in a 3 L flask. With stirring, the flask was heated to 52° C. for 16 hours. At the end of this time, potassium hydroxide (52 grams, dissolved in 300 g water) was added, and the resulting mixture was heated to 65° C. and then distilled azeotropically using a Dean Stark trap, from which the resulting lower fluorochemical phase was separated during the distillation. The resulting product was distilled (b.p.=189-191° C.) to a purity of 92 percent. Product structure was confirmed by IR and GCMS.

Example 11

Preparation of $C_3F_7OCF(CF_3)CF(OC_2H_5)C_4F_9$

Perfluorovaleryl fluoride, $C_4F_9C(O)F$, was prepared by electrochemical fluorination of $HCF_2CF_2CF_2CH_2OH$. The acyl fluoride from the cell was purified by fractional distillation to obtain 91.4 percent perfluorovaleryl fluoride. This material was used in subsequent reactions without further purification. As used herein, the term "perfluorovaleryl fluoride" refers to this material.

A clean, dry, 600 mL, stainless steel, Parr pressure reactor was charged with spray-dried potassium fluoride (8.4 grams, 0.14 mole), anhydrous diglyme (128 grams), and Adogen™ 464 phase transfer catalyst (2.2 grams). The reactor was sealed, cooled with a dry ice-acetone bath, evacuated, and charged with perfluorovaleryl fluoride (130.0 grams, 0.49 mole) and $C_3F_7OCF=CF_2$ (125.0 grams, 0.47 mole). The reactor was then heated to 85° C. and held for 20 hours with agitation. The reactor was cooled to below 0° C. with a dry ice-acetone bath and vented. The reactor contents were added to a clean, dry 2 L round bottom flask equipped with a mechanical stirrer, a heating mantle, a temperature probe, and a water condenser. The flask was charged with spray-dried potassium fluoride (16.0 grams, 0.28 mole), diethyl sulfate (61.0 grams, 0.40 mole), anhydrous diglyme (48 grams), and catalyst (2.5 grams). The contents of the flask were stirred, heated to 52° C., and held for 20 hours. The flask was cooled to ambient temperature, and water (35 grams) and 45 percent KOH (75 grams, 0.60 mole) were added. The flask was heated to 65° C. and held for 4 hours to neutralize excess diethyl sulfate. The resulting crude product was isolated by steam distillation, washed one time with an equal weight of water, and fractionally distilled to provide 91.0 grams of 99.3 percent purity product $C_3F_7OCF(CF_3)CF(OC_2H_5)C_4F_9$. The boiling point of this product was 178° C., and its structure was confirmed by GCMS. The viscosity of the product was 7.3× $10^{-5}$ m$^2$/s (73 centistokes) at −50° C. (measured using a Cannon-Fenske viscometer and a Wescan Model 221 viscosity timer).

Example 12

Preparation of $C_3F_7OCF(CF_3)CF(OC_2H_5)CF(CF_3)$
$OC_3F_7$

A clean, dry, 600 mL, stainless steel, Parr pressure reactor was charged with spray-dried potassium fluoride (7.5 grams, 0.13 mole) and anhydrous diglyme (105 grams). The reactor was sealed, cooled with a dry ice-acetone bath, evacuated, and charged with perfluoropropionyl fluoride (191.0 grams, 1.15 mole). The reactor was heated to −15° C., and hexafluoropropylene oxide (109 grams, 0.66 mole) was added over a 1.25 hour period, keeping the temperature below 0° C. The reactor was held an additional 30 minutes at −10° C., and then excess perfluoropropionyl fluoride was vented through a methanol scrubber as the temperature was slowly raised to 40° C. The reactor was cooled to 5° C., opened, and charged with $C_3F_7OCF=CF_2$ (220 grams, 0.83 mole), anhydrous diglyme (12 grams), and Adogen™ phase transfer catalyst (4.5 grams). The reactor was then heated to 85° C. and held for 22 hours with agitation. The reactor was cooled to room temperature and vented. The reactor contents were added to a clean dry two liter round bottom flask equipped with a mechanical stirrer, a heating mantle, a temperature probe, and a water condenser. The flask was charged with spray-dried potassium fluoride (58.7 grams, 1.01 mole), diethyl sulfate (172.0 grams, 1.11 mole), anhydrous diglyme (100 grams), and catalyst (5.8 grams). The flask contents were stirred, heated to 52° C., and held for 112 hours. The flask was cooled to ambient temperature, and water (262 grams) and 45 percent KOH (210 grams, 1.68 mole) were added. The flask was heated to 65° C. and held for 4 hours to neutralize excess diethyl sulfate. The resulting crude product was isolated by steam distillation and washed one time with an equal weight of water to provide 441.1 grams of product with a purity of 35.1 percent as determined by GC analysis. The product yield based on this GC analysis, as well as the limiting reagent of hexafluoropropene oxide, was 36.6 percent. The product was fractionally distilled to provide 52.3 grams of 99.7 percent purity product $C_3F_7OCF(CF_3)CF(OC_2H_5)CF(CF_3)OC_3F_7$. The boiling point of this product was 190° C., and its structure was confirmed by GCMS. The viscosity of this product was $12.0 \times 10^{-5}$ m$^2$/s (120 centistokes) at −5° C. (measured using a Cannon-Fenske viscometer and a Wescan Model 221 viscosity timer).

Example 13

Preparation of $CF_3OC_3F_6CF(CF_3)CF(OC_2H_5)$ $C_2F_4OCF_3$

Tetrafluoro-3-trifluoromethoxy propionyl fluoride, $CF_3OC_2F_4C(O)F$, was prepared by electrochemical fluorination of $CH_3OCF_2CF_2C(O)OCH_3$. The acyl fluoride from the cell was purified by fractional distillation to obtain 85.0 percent tetrafluoro-3-trifluoromethoxy propionyl fluoride. This material was used in subsequent reactions without further purification. As used herein, the term "tetrafluoro-3-trifluoromethoxy propionyl fluoride" refers to this material.

A clean, dry, 600 mL, stainless steel, Parr pressure reactor was charged with spray-dried potassium fluoride (12.0 grams, 0.20 mole), anhydrous diglyme (130 grams), and Adogen™ 464 phase transfer catalyst (4.7 grams). The reactor was sealed, cooled with a dry ice-acetone bath, evacuated, and charged with $CF_3OC_2F_4C(O)F$ (110 grams, 0.47 mole) and $CF_3OC_3F_6OCF=CF_2$ (130.0 grams, 93 percent purity, 0.39 mole). The reactor was then heated to 85° C. and held for 29 hours with agitation. The reactor was cooled to room temperature and vented. The reactor contents were added to a clean dry two liter round bottom flask equipped with a mechanical stirrer, a heating mantle, a temperature probe, and a water condenser. The flask was charged with spray-dried potassium fluoride (34.4 grams, 0.59 mole), diethyl sulfate (100.7 grams, 0.65 mole), anhydrous diglyme (105 grams), and catalyst (6.4 grams). The flask contents were stirred, heated to 52° C., and held for 40 hours. The flask was cooled to ambient temperature, and water (150 grams) and 45 percent KOH (120 grams, 0.96 mole) were added. The flask was heated to 65° C. and held for 4 hours to neutralize excess diethyl sulfate. The resulting crude product was isolated by steam distillation and washed one time with an equal weight of water to provide 230.0 grams of product with a purity of 65.3 percent as determined by GC analysis. The product was fractionally distilled to provide 136.0 grams of 99.5 percent purity product $CF_3OC_3F_6CF(CF_3)CF(OC_2H_5)C_2F_4OCF_3$. The boiling point of this product was 181° C., and its structure was confirmed by GCMS. The viscosity of this product was $3.4 \times 10^{-5}$ m$^2$/s (34 centistokes) at −50° C. (measured using a Cannon-Fenske viscometer and a Wescan Model 221 viscosity timer).

Comparative Example A

Preparation of $(CF_3)_2CFCF(OC_2H_5)CF(CF_3)_2$ 302 grams (0.83 mole) of a ketone mixture of 96.0 percent $(CF_3)_2CFC(O)CF(CF_3)_2$ and 4.0 percent $CF_3CF_2CFC(O)CF(CF_3)_2$, 300 mL anhydrous 1,2-dimethoxyethane, 59.5 grams (1.02 mole) potassium fluoride, 11.1 grams Adogen™ 464 phase transfer catalyst, and 174 grams (1.12 mole) diethyl sulfate were combined in a 2 L flask and heated with stirring to 52° C. for 89 hours. At the end of the 89 hours, the flask was cooled to room temperature, and 230 grams of 45 percent potassium hydroxide and 95 grams of water were added. The resulting mixture was distilled azeotropically using a Dean Stark trap, from which the resulting lower fluorochemical phase was separated during the distillation. The fluorochemical phase was washed twice with an equal volume of water and dried over magnesium sulfate. 53.0 grams of material resulted, with a purity of 37.6 percent $(CF_3)_2CFCF(OC_2H_5)CF(CF_3)_2$ (yield of 6.1 percent; structure confirmed by GCMS).

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A hydrofluoroether compound, wherein said compound is one of a class that is represented by the following general formula (I):

R′$_f$—CFX—O—CF(CF$_3$)—CF(OR)—CFX′—R″$_f$  (I)

wherein R′$_f$ is a perfluoroalkyl group that is linear, branched, cyclic, or a combination thereof, that optionally contains at least one catenated heteroatom, and that optionally comprises a terminal moiety selected from —CF$_2$H, —CFHCF$_3$, and —CF$_2$OCH$_3$; R″$_f$ is a fluorine atom or a perfluoroalkyl group that is linear, branched, cyclic, or a combination thereof, that optionally contains at least one catenated heteroatom, and that optionally comprises a terminal moiety selected from —CF$_2$H, —CFHCF$_3$, and —CF$_2$OCH$_3$; X is a fluorine atom or a perfluoroalkyl group that is linear, branched, cyclic, or a combination thereof and that has from one to about six carbon atoms; X′ is a fluorine atom or a perfluoroalkyl group that is linear, branched, cyclic, or a combination thereof and that has from one to about six carbon atoms; and R is an alkyl or fluoroalkyl group that is linear, branched, cyclic, or a combination thereof and that optionally contains at least one catenated heteroatom; wherein said compound comprises at least one perfluoromorpholino moiety.

2. The hydrofluoroether compound of claim 1, wherein said R′$_f$ is a perfluoroalkyl group that is linear or branched, that optionally contains at least one catenated heteroatom, and that has from one to about eight carbon atoms; said $R''_f$ is a fluorine atom or a perfluoroalkyl group that is linear or branched, that optionally contains at least one catenated heteroatom, and that has from one to about eight carbon atoms; said X is a fluorine atom or a perfluoroalkyl group that is linear or branched and that has from one to about three carbon atoms; said X' is a perfluoroalkyl group that is linear or branched and that has from one to about three carbon atoms; and said R is an alkyl or fluoroalkyl group that is linear or branched and that has from one to about eight carbon atoms.

3. The hydrofluoroether compound of claim 2, wherein said $R'_f$ is a perfluoroalkyl group that is linear or branched, that optionally contains at least one catenated heteroatom, and that has from one to about four carbon atoms; said $R''_f$ is a fluorine atom or a perfluoroalkyl group that is linear or branched, that optionally contains at least one catenated heteroatom, and that has from one to about four carbon atoms; said X is a fluorine atom or a perfluoromethyl group; said X' is a perfluoromethyl group; and said R is an alkyl group having from one to about four carbon atoms.

4. The hydrofluoroether compound of claim 3, wherein said R is an ethyl or methyl group.

5. The hydrofluoroether compound of claim 1, wherein said X' is perfluoroalkyl.

6. A hydrofluoroether compound, wherein said compound is one of a class that is represented by the following general formula (I):

wherein $R'_f$ is a perfluoroalkyl group that is linear, branched, cyclic, or a combination thereof, that optionally contains at least one catenated heteroatom, and that optionally comprises a terminal moiety selected from —$CF_2H$, —$CFHCF_3$, and —$CF_2OCH_3$; $R''_f$ is a fluorine atom or a perfluoroalkyl group that is linear, branched, cyclic, or a combination thereof, that optionally contains at least one catenated heteroatom, and that optionally comprises a terminal moiety selected from —$CF_2H$, —$CFHCF_3$, and —$CF_2OCH_3$; X is a fluorine atom or a perfluoroalkyl group that is linear, branched, cyclic, or a combination thereof and that has from one to about six carbon atoms; X' is a fluorine atom or a perfluoroalkyl group that is linear, branched, cyclic, or a combination thereof and that has from one to about six carbon atoms; and R is an alkyl or fluoroalkyl group that is linear, branched, cyclic, or a combination thereof and that optionally contains at least one catenated heteroatom; with the proviso that when X' is a fluorine atom, said compound comprises at least one perfluoromorpholino moiety; and said compound is selected from the following, where R is selected from $CH_3$ and $C_2H_5$:

$C_2F_5OCF(CF_3)CF(OR)CF(CF_3)_2$  $C_2F_5OCF(CF_3)CF(OR)CF(CF_3)OC_3F_7$  $C_2F_5OCF(CF_3)CF(OR)CF(CF_3)OC_2F_5$

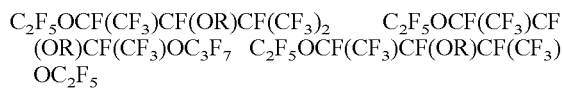

$CF_3CF_2CF_2OCF(CF_3)CF(OR)CF(CF_3)_2$
$CF_3CF_2CF_2OCF(CF_3)CF(OR)CF(CF_3)OC_3F_7$

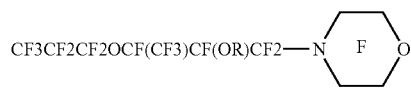

$CF_3CF_2CF_2CF_2OCF(CF_3)CF(OR)CF(CF_3)_2$
$CF_2CF_2CF_2CF_2OCF(CF_3)CF(OR)CF(CF_3)OC_3F_7$
$CF_2CF_2CF_2CF_2OCF(CF_3)CF(OR)CF(CF_3)OC_4F_9$

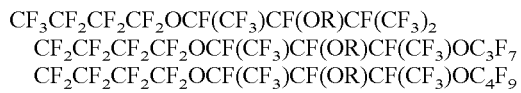

$(CF_3)_2CFCF_2OCF(CF_3)CF(OR)CF(CF_3)_2$, $(CF_3)_2CFCF_2OCF(CF_3)CF(OR)CF(CF_3)OC_3F_7$ $(CF_3)_2CFCF_2OCF(CF_3)CF(OR)CF(CF_3)OC_4F_9$

$CF_3OCF_2CF_2CF_2OCF(CF_3)CF(OR)CF(CF_3)_2$
$CF_3OCF_2CF_2CF_2OCF(CF_3)CF(OR)CF(CF_3)OC_3F_7$
$CF_3OCF_2CF_2CF_2OCF(CF_3)CF(OR)CF(CF_3)OCF_2CF_2CF_2OCF_3$

$C_5F_{11}OCF(CF_3)CF(OR)CF(CF_3)_2$  $C_5F_{11}OCF(CF_3)CF(OR)CF(CF_3)OC_3F_7$  $C_5F_{11}OCF(CF_3)CF(OR)CF(CF_3)OC_4F_9$

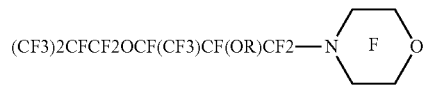
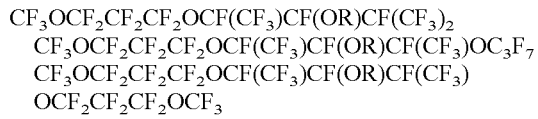
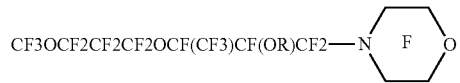
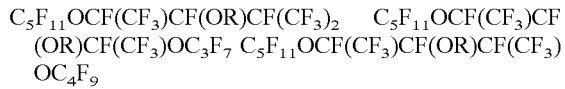
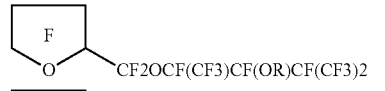
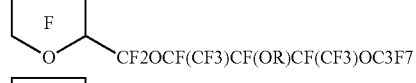
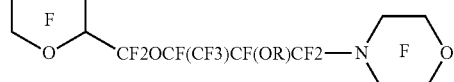
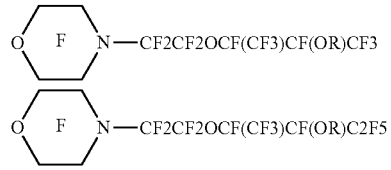

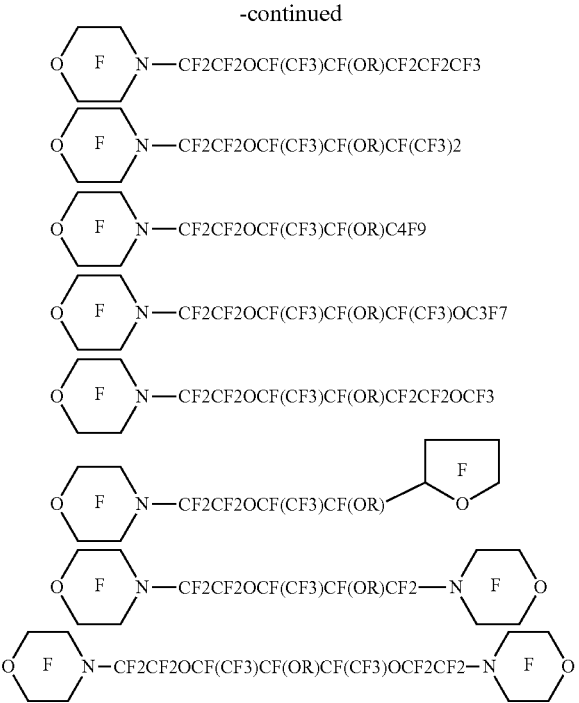

$C_3F_7OCF(CF_3)CF_2OCF(CF_3)CF(OR)CF(CF_3)_2$
$C_3F_7OCF(CF_3)CF_2OCF(CF_3)CF(OR)CF(CF_3)OC_3F_7$
$C_3F_7OCF(CF_3)CF_2OCF(CF_3)CF(OR)CF(CF_3)$
$OCF_2CF(CF_3)OC_3F_7$

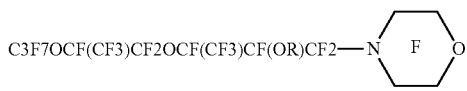

and mixtures thereof.

7. A process for preparing the hydrofluoroether compound of claim 6 comprising (a) reacting at least one fluorochemical acid fluoride with at least one fluoro- or perfluorovinyl ether to form at least one fluorochemical ketone comprising two terminal, independently fluoroalkyl or perfluoroalkyl groups and an intervening oxytetrafluoroethylidene moiety (—OCF$(CF_3)$—) bonded through its central carbon atom to a carbonyl group, each of said terminal groups optionally comprising at least one catenated heteroatom; (b) reacting said fluorochemical ketone compound with at least a stoichiometric amount of at least one fluoride source to form at least one fluorochemical alkoxide; and (c) reacting said fluorochemical alkoxide with at least one alkylating agent to form at least one hydrofluoroether compound of claim 6.

8. The process of claim 7, wherein said fluorochemical ketone comprises at least one perfluoromorpholino moiety.

9. The process of claim 7, wherein said fluorochemical ketone comprises branched moieties on both sides of, and adjacent to, its carbonyl group.

10. A process for removing a contaminant from an article comprising contacting said article with a composition comprising at least one hydrofluoroether compound of claim 6.

11. A process for preparing a foamed plastic comprising vaporizing a blowing agent mixture in the presence of at least one foamable polymer or the precursors of at least one foamable polymer, said blowing agent mixture comprising at least one hydrofluoroether compound of claim 6.

12. A process for vapor phase soldering comprising melting solder by immersing at least one component that comprises said solder in a body of fluorochemical liquid vapor that comprises at least one hydrofluoroether compound of claim 6.

13. A process for transferring heat comprising transferring heat between a heat source and a heat sink through the use of a heat transfer agent comprising at least one hydrofluoroether compound of claim 6.

14. A process for depositing a coating on a substrate comprising applying to at least a portion of at least one surface of said substrate a composition comprising (a) a solvent composition comprising at least one hydrofluoroether compound of claim 6; and (b) at least one coating material that is soluble or dispersible in said solvent composition.

15. A process for cutting or abrasive working comprising applying a working fluid to a metal, cermet, or composite workpiece and tool, said working fluid comprising at least one hydrofluoroether compound of claim 6 and at least one lubricious additive.

16. A polymerization process comprising polymerizing at least one monomer in the presence of at least one polymerization initiator and at least one hydrofluoroether compound of claim 6.

* * * * *

UNITED STATES PATENT AND TRADEMARK OFFICE
CERTIFICATE OF CORRECTION

PATENT NO. : 8,193,397 B2
APPLICATION NO. : 11/567643
DATED : June 5, 2012
INVENTOR(S) : Richard M. Flynn It is certified that error appears in the above-identified patent and that said Letters Patent is hereby corrected as shown below:

In the Specifications:

Column 11
Lines 64-55, delete

"  "

and insert

-- 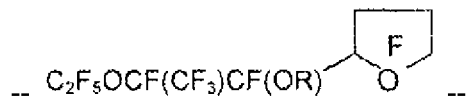 --

Column 17
Line 21, delete "phophonium" and insert --phosphonium--

Column 35
Line 27, delete "–5°C" and insert -- –50°C--

Signed and Sealed this
Thirty-first Day of July, 2012

David J. Kappos
*Director of the United States Patent and Trademark Office*